(12) United States Patent
Shiina

(10) Patent No.: US 9,796,640 B2
(45) Date of Patent: Oct. 24, 2017

(54) METHOD FOR PRODUCING OPTICALLY ACTIVE CARBOXYLIC ACID ESTER

(71) Applicant: TOKYO UNIVERSITY OF SCIENCE FOUNDATION, Shinjuku-ku, Tokyo (JP)

(72) Inventor: Isamu Shiina, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 0 days.

(21) Appl. No.: 15/115,764

(22) PCT Filed: Feb. 2, 2015

(86) PCT No.: PCT/JP2015/052882
§ 371 (c)(1),
(2) Date: Aug. 1, 2016

(87) PCT Pub. No.: WO2015/115650
PCT Pub. Date: Aug. 6, 2015

(65) Prior Publication Data
US 2017/0008820 A1    Jan. 12, 2017

(30) Foreign Application Priority Data

Feb. 3, 2014 (JP) .................................. 2014-018887

(51) Int. Cl.
| | |
|---|---|
| *C07B 53/00* | (2006.01) |
| *C07C 269/06* | (2006.01) |
| *C07D 235/06* | (2006.01) |
| *C07D 403/06* | (2006.01) |
| *C07D 471/04* | (2006.01) |
| *C07D 263/58* | (2006.01) |
| *C07D 207/27* | (2006.01) |
| *C07C 271/22* | (2006.01) |
| *C07B 55/00* | (2006.01) |
| *C07D 207/327* | (2006.01) |
| *C07D 207/333* | (2006.01) |
| *C07D 207/416* | (2006.01) |
| *C07D 209/08* | (2006.01) |
| *C07D 209/12* | (2006.01) |
| *C07D 209/34* | (2006.01) |
| *C07D 209/38* | (2006.01) |
| *C07D 513/04* | (2006.01) |
| *C07D 209/48* | (2006.01) |
| *C07D 209/86* | (2006.01) |
| *C07D 207/34* | (2006.01) |

(52) U.S. Cl.
CPC .............. *C07B 53/00* (2013.01); *C07B 55/00* (2013.01); *C07C 269/06* (2013.01); *C07D 207/27* (2013.01); *C07D 207/327* (2013.01); *C07D 207/333* (2013.01); *C07D 207/34* (2013.01); *C07D 207/416* (2013.01); *C07D 209/08* (2013.01); *C07D 209/12* (2013.01); *C07D 209/34* (2013.01); *C07D 209/38* (2013.01); *C07D 209/48* (2013.01); *C07D 209/86* (2013.01); *C07D 235/06* (2013.01); *C07D 263/58* (2013.01); *C07D 403/06* (2013.01); *C07D 471/04* (2013.01); *C07D 513/04* (2013.01); *C07B 2200/07* (2013.01)

(58) Field of Classification Search
None
See application file for complete search history.

(56) References Cited

U.S. PATENT DOCUMENTS

| | | |
|---|---|---|
| 2010/0234610 A1 | 9/2010 | Shiina et al. |
| 2014/0135520 A1 | 5/2014 | Shiina et al. |

FOREIGN PATENT DOCUMENTS

| | | |
|---|---|---|
| JP | 5417560 B2 | 2/2014 |
| WO | 2008140074 A1 | 11/2008 |
| WO | 2009113428 A1 | 9/2009 |
| WO | 2012169575 A1 | 12/2012 |

OTHER PUBLICATIONS

Kashima C et al: "Peptide Synthesis Using the Pyrrole Ring as an Amino Protecting Group", Journal of Chemical Research. Miniprint, Scientific Reviews, Northwood, GB, vol. 2, Jan. 1, 1988 (Jan. 1, 1988), pp. 601-645, XP009065887.

Supplementary European search report for European Patent Application No. 15743807.8 dated Oct. 19, 2016.

Atsushi Tengeji et al., "Racemic Amino San Hogotai no Doteki Sokudoron-teki Kogaku Bunkatsu ni yoru Kogaku Kassei Amino San no Gosei", CSJ: The Chemical Society of Japan Dai 94 Shunki Nenkai (2014) Koen Yokoshu IV, Mar. 12, 2014, p. 1358, 1 B7-11.

Ken'ya Nakata et al., "Racemic-2-Amino-2-Aryl Sakusan-rui no Seiteki Oyobi Doteki Sokudoron Kogaku Bunkatsu Hanno no Kaihatsu", CSJ: The Cehmical Society of Japan Dai 93 Shunki Nenkai (2013) Koen Yokoshu IV, Mar. 8, 2013 (Mar. 8, 2013), p. 1371, 3 E5-49.

(Continued)

*Primary Examiner* — Samantha Shterengarts
(74) *Attorney, Agent, or Firm* — Cantor Colburn LLP

(57) ABSTRACT

Provided is a method for producing an optically active carboxylic acid ester at a high yield and with high enantioselectivity using dynamic kinetic resolution, said optically active carboxylic acid ester having an α-nitrogen substituent. This method for producing an optically active carboxylic acid ester includes a step in which racemic carboxylic acid represented by formula (a) and a specific alcohol or phenol derivative are reacted in a polar solvent having a dipole moment of at least 3.5 in the presence of an acid anhydride and an asymmetric catalyst, one enantiomer of the racemic carboxylic acid is selectively esterified, and the other enantiomer is racemized. In formula (a), Ra1 represents a nitrogen-containing heteroaromatic ring group bonded to an assymetric carbon via a nitrogen atom constituting a ring, and Ra2 is an organic group.

10 Claims, No Drawings

(56) References Cited

OTHER PUBLICATIONS

Takayoshi Nakahara et al., "Racemic Amino San Hogotai no Doteki Sokudoron Kogaku Bunkatsu ni yoru Kogaku Kassei Amino San no Gosei", Dai 106 Kai Symosium on Organic Synthesis, Japan Yoshishu, Oct. 27, 2014 (Oct. 27, 2014), pp. 74 to 75.
Yang, X. et al, Kinetic Resolution of α-Substituted Alkanoic Acids Promoted by Homobenzotetramisole. Chemistry—A European Journal, 2011, vol. 17, No. 40, p. 11296-11304, entire text.
International Search Report corresponding to Application No. PCT/JP2015/052882; dated Apr. 21, 2015, with English translation.

METHOD FOR PRODUCING OPTICALLY ACTIVE CARBOXYLIC ACID ESTER

CROSS REFERENCE TO RELATED APPLICATIONS

This is the U.S. national stage of application No. PCT/JP2015/052882 filed on Feb. 2, 2015. Priority under 35 U.S.C. §119(a) and 35 U.S.C. §365(b) is claimed from Japanese Application No. 2014-018887, filed Feb. 3, 2014, the disclosure of which is also incorporated herein by reference.

TECHNICAL FIELD

The present invention relates to a method for producing an optically active carboxylic acid ester using dynamic kinetic resolution.

BACKGROUND ART

Optically active carboxylic acid esters are used in various fields as pharmaceuticals, intermediates of physiologically active substances, and intermediates in the synthesis of natural products.

Hitherto, a method by reacting a carboxylic acid with an alcohol using an asymmetric catalyst is a known method for producing optically active carboxylic acid esters. For example, a method is proposed in Patent Document 1 in which an optically active carboxylic acid ester is produced by reacting racemic carboxylic acids with an alcohol in the presence of benzoic anhydride or a derivative thereof by using tetramisole or benzo-tetramisole as a catalyst.

However, in the kinetic resolution as described in Patent Document 1, one enantiomer of the racemic carboxylic acids to be the raw material is selectively esterified, and thus the yield of the optically active carboxylic acid ester is theoretically a maximum of 50%.

Hence, a method for producing an optically active carboxylic acid ester using the dynamic kinetic resolution is proposed in Patent Document 2. According to the method described in Patent Document 2, it is possible to produce an optically active carboxylic acid ester at a high yield of over 50% by increasing the amount of carboxylic acid to be esterified through racemization of the optically active carboxylic acid that is the other enantiomer as well as by producing an optically active carboxylic acid ester through selective esterification of one enantiomer of the racemic carboxylic acids.

Patent Document 1: PCT International Publication No. WO2009/113428
Patent Document 2: PCT International Publication No. WO2012/169575

DISCLOSURE OF THE INVENTION

Problems to be Solved by the Invention

Meanwhile, α-amino acids are regarded as a fundamental compound in the natural science related to the living body, and a method for producing an optically active α-amino acid and derivatives thereof at a high yield is desired.

However, it is difficult to produce an optically active α-amino acid ester by using racemic α-amino acids as a raw material by the method described in Patent Document 2. This is because the acidity of α-proton of α-amino acids is low and it is difficult to promptly racemize an optically active α-amino acid. In addition, it has been confirmed by the present inventors that it is not possible to obtain an optically active α-amino acid ester of which the amino group is protected at a high yield and with high enantioselectivity even though the amino group of the α-amino acid is protected with a protective group such as Boc.

The present invention has been made in view of such problems, and an object thereof is to provide a method for producing an optically active carboxylic acid ester having an α-nitrogen substituent at a high yield and with high enantioselectivity by using dynamic kinetic resolution.

Means for Solving the Problems

The present inventors have carried out intensive investigations to solve the above problems. As a result, it has been found out that it is possible to produce an optically active carboxylic acid ester at a high yield and with high enantioselectivity by using racemic carboxylic acids having a nitrogen-containing heteroaromatic ring group as an α-nitrogen substituent. In addition, it has been found out that it is possible to use a 1H-pyrrol-1-yl group among the nitrogen-containing heteroaromatic ring groups as the protective group of an amino group. The present invention is based on such findings, and it is more specifically as follows.

(1) A method for producing an optically active carboxylic acid ester by dynamic kinetic resolution, the method including a step of racemizing the other enantiomer of racemic carboxylic acids represented by the following formula (a):

[in formula (a), Ra1 represents a nitrogen-containing heteroaromatic ring group bonded to an asymmetric carbon via a nitrogen atom constituting a ring, and Ra2 represents an organic group.]

as well as selectively esterifying one enantiomer of the racemic carboxylic acids by reacting the racemic carboxylic acids with an alcohol represented by the following formula (b):

[in formula (b), Rb represents a phenyl group, naphthyl group, anthryl group, or phenanthryl group which optionally has a substituent.]

or a phenol derivative represented by the following formula (c):

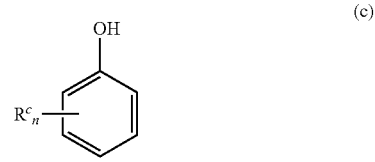

[in formula (c), Rc represents a phenyl group, naphthyl group, anthryl group, or phenanthryl group which optionally has a substituent, and n represents an integer from 1 to 5. Rcs may be the same as or different from one another in a case in which there are a plurality of Rcs.]

in a polar solvent having a dipole moment of 3.5 or more in the presence of an acid anhydride and an asymmetric catalyst.

(2) The method for producing an optically active carboxylic acid ester according to (1), in which the asymmetric catalyst is represented by any one of the following formulas (d) to (g):

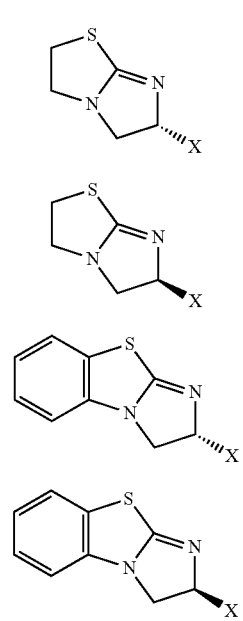

[in formulas (d) to (g), X represents any one of the following substituents,

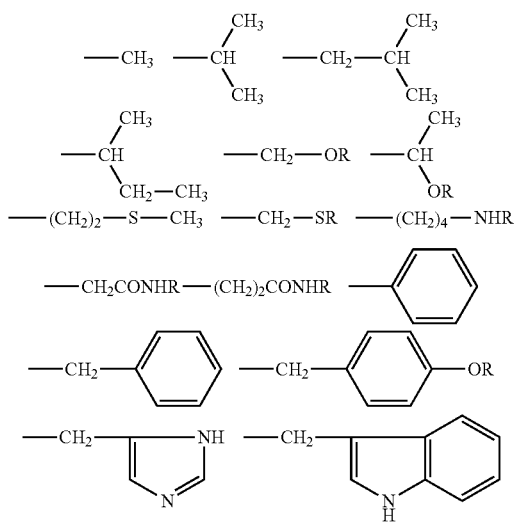

and R represents a protective group of a hydroxyl group.]

(3) The method for producing an optically active carboxylic acid ester according to (1) or (2), in which Ra1 in formula (a) is a 1H-pyrrol-1-yl group.

(4) The method for producing an optically active carboxylic acid ester according to any one of (1) to (3), in which the polar solvent having a dipole moment of 3.5 or more is dimethylacetamide, dimethylformamide, 1,3-dimethyl-2-imidazolidinone, N-methylpyrrolidone, or dimethyl sulfoxide.

(5) The method for producing an optically active carboxylic acid ester according to any one of (1) to (4), in which the step is performed in the presence of a base.

(6) The method for producing an optically active carboxylic acid ester according to (5), in which the base is represented by the following formula (i):

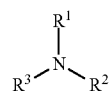

[in formula (i), in formula (i), R1, R2, and R3 independently represent an alkyl group having from 1 to 8 carbon atoms.].

(7) The method for producing an optically active carboxylic acid ester according to (6), in which at least one of R1, R2, or R3 is a methyl group.

(8) The method for producing an optically active carboxylic acid ester according to (6), in which the base is diisopropylethylamine, triethylamine, dimethylethylamine, dimethylisopropylamine, diethylmethylamine, or diisopropylmethylamine.

(9) The method for producing an optically active carboxylic acid ester according to any one of (1) to (8), further including a step of obtaining racemic carboxylic acids represented by formula (a) by converting an amino group of racemic α-amino acids represented by the following formula (h):

[in formula (h), Ra2 is synonymous with that in formula (a).]

into a 1H-pyrrol-1-yl group.

(10) The method for producing an optically active carboxylic acid ester according to any one of (1) to (9), further including a step of converting a 1H-pyrrol-1-yl group of an optically active carboxylic acid ester obtained by dynamic kinetic resolution into an amino group.

Effects of the Invention

According to the present invention, it is possible to provide a method for producing an optically active carboxylic acid ester having an α-nitrogen substituent at a high yield and with high enantioselectivity by using dynamic kinetic resolution.

PREFERRED MODE FOR CARRYING OUT THE INVENTION

Racemic Carboxylic Acids

The racemic carboxylic acids to be used in the production method according to the present invention are represented by the following formula (a).

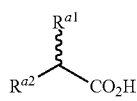

(a)

In formula (a), Ra1 represents a nitrogen-containing heteroaromatic ring group bonded to an asymmetric carbon via a nitrogen atom constituting a ring. Examples of the nitrogen-containing heteroaromatic ring group may include a 1H-pyrrol-1-yl group, a 1H-indol-1-yl group, a 1H-benzo[d]imidazol-1-yl group, a 9H-carbazol-9-yl group, a 1H-imidazol-1-yl group, a 1H-pyrazol-1-yl group, a 1H-cyclopenta[b]pyridin-1-yl group, a 2H-isoindol-2-yl group, a 1H-indazol-1-yl group, a 7H-purine-7-yl group, a 10H-phenoxazine-10-yl group, a 10H-phenothiazine-10-yl group, and a 3H-3-benzazepine-3-yl group. This nitrogen-containing heteroaromatic ring group optionally has an arbitrary substituent such as an alkyl group, an aryl group, an alkoxy group, an alkylcarbonyl group, a cyano group, or a halogen atom on the ring, but it is preferable that this nitrogen-containing heteroaromatic ring group is unsubstituted. Among these nitrogen-containing heteroaromatic ring groups, a 1H-pyrrol-1-yl group and a 1H-indol-1-yl group are more preferable, and a 1H-pyrrol-1-yl group is particularly preferable.

In formula (a), Ra2 represents an organic group. Examples of the organic group may include an alkyl group, an alkenyl group, an alkynyl group, an aryl group, a heteroaryl group, an alkoxyalkyl group, an alkoxyalkenyl group, an alkoxyalkynyl group, an arylalkyl group, an arylalkenyl group, an arylalkynyl group, a heteroarylalkyl group, a heteroarylalkenyl group, a heteroarylalkynyl group, an alkylaryl group, an alkylheteroaryl group, an alkoxyaryl group, and an alkoxyheteroaryl group, and these groups are optionally substituted with a group other than the organic groups such as a halogen atom, an aryl group such as phenyl or naphthyl, or a heteroaryl group such as thiophene, imidazole, or indole. Among these, a group which does not have a branch at the β-position is preferred to a group which has a branch at the β-position such as an isopropyl group or a phenyl group.

Among the nitrogen-containing heteroaromatic ring groups described above, it is possible to use a 1H-pyrrol-1-yl group as a protective group of an amino group. For example, the racemic carboxylic acids represented by formula (a) can be obtained by converting the amino group into a 1H-pyrrol-1-yl group by the Clauson-Kaas synthesis method in which the racemic α-amino acids represented by the following formula (h) and 2,5-dialkoxytetrahydrofuran are refluxed (see K. Kashima et al., J. Chem. Res. Miniprint, 1988, 601-645, and the like). Incidentally, in formula (h), Ra2 is synonymous with that in formula (a).

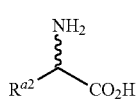

(h)

In addition, after the optically active carboxylic acid ester is obtained by using dynamic kinetic resolution, the 1H-pyrrol-1-yl group can be converted into an amino group, for example, by ozonolysis (see K. Kashima et al., J. Chem. Soc. Perkin Trans. 1, 1989, 1041-1046, and the like).

[Alcohol]

The alcohol to be used in the production method according to the present invention is represented by the following formula (b).

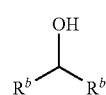

(b)

In formula (b), Rb represents a phenyl group, naphthyl group, anthryl group, or phenanthryl group which optionally has a substituent. Examples of the substituent of Rb may include an alkyl group, an alkoxy group, an aryl group, and a halogen atom. Particularly, a 2-tolyl group, a 1-naphthyl group, and a 9-phenanthryl group are preferable as Rb. By using such an alcohol, it is possible to produce an optically active carboxylic acid ester having high enantioselectivity.

[Phenol Derivative]

The phenol derivative to be used in the production method according to the present invention is represented by the following formula (c).

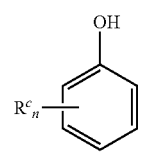

(c)

In formula (c), Rc represents a phenyl group, naphthyl group, anthryl group, or phenanthryl group which optionally has a substituent, and a naphthyl group is preferable. Examples of the substituent of Rc may include an alkyl group, an alkoxy group, an aryl group, and a halogen atom. n is an integer from 1 to 5, and it is preferable that n=2. Rcs may be the same as or different from one another in a case in which there are a plurality of Rcs. Among such phenol derivatives, those obtained by substituting the second and sixth positions of a phenol with a naphthyl group are preferable.

[Acid Anhydride]

The acid anhydride to be used in the production method according to the present invention acts as a dehydrating and condensing agent. As the acid anhydride, those obtained from benzoic acid, benzoic acid in which an electron-donating group such as an alkyl group, an alkoxy group, an amino group, or an alkoxyalkyl group is bonded to a phenyl group, or a multi-substituted carboxylic acid of which the α-position is a quaternary carbon is preferable, and those obtained from benzoic acid, 1 to 3-substituted benzoic acid to which an alkyl group or alkoxy group which has from 1 to 3 carbon atoms is bonded, pivalic acid, 2-methyl-2-phenylpropionic acid, or 2,2-diphenylpropionic acid is more preferable.

[Asymmetric Catalyst]

The asymmetric catalyst to be used in the production method according to the present invention is not particularly limited, but those represented by the following formulas (d) to (g) are preferable.

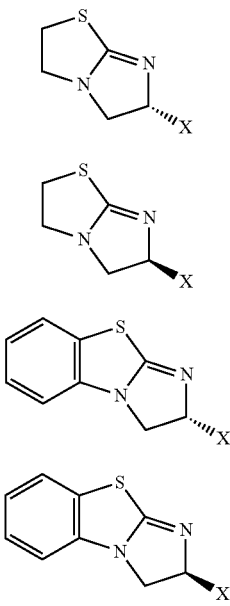

d e f g

In formulas (d) to (g), X represents any one of the following substituents. R is a protective group of a hydroxyl group, and examples thereof may include an alkyl group, an acyl group, and a silyl group.

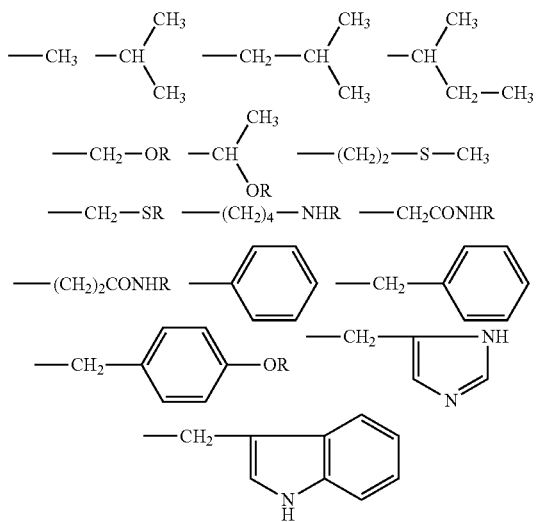

Among the asymmetric catalysts represented by formulas (d) to (g), the catalyst that is represented by formula (d) or (e) in which X is a phenyl group is referred to as tetramisole, the catalyst that is represented by formula (f) or (g) in which X is a phenyl group is referred to as benzo-tetramisole. These catalysts are available as commercial products or can be synthesized by using an amino acid having a substituent represented by X as a side chain.

[Polar Solvent]

The polar solvent to be used in the production method according to the present invention has a dipole moment of 3.5 or more. Examples of such a polar solvent may include N,N-dimethylacetamide, N,N-dimethylformamide, 1,3-dimethyl-2-imidazolidinone, N-methylpyrrolidone, dimethyl sulfoxide, nitrobenzene, pyridazine, benzonitrile, and propionitrile. By using a polar solvent having a dipole moment of 3.5 or more, the racemization of an optically active carboxylic acid that is not the target of esterification is likely to occur.

[Reaction Conditions and the Like]

The production of an optically active carboxylic acid ester is carried out by adding racemic carboxylic acids, an alcohol or a phenol derivative, an acid anhydride, and an asymmetric catalyst into a polar solvent, but it is preferable to add a base to the reaction system. As this base, an organic base which does not exhibit nucleophilicity is preferable, and an amine represented by the following formula (i):

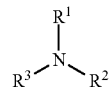

[in formula (i), R1, R2, and R3 independently represent an alkyl group having from 1 to 8 carbon atoms.]

is more preferable. R1, R2, and R3 are not particularly limited as long as they are an alkyl group having from 1 to 8 carbon atoms, but it is preferable that at least one of R1, R2, or R3 is a methyl group.

Examples of the amine represented by formula (i) may include trimethylamine, triethylamine, diisopropylethylamine, dimethylethylamine, dimethylisopropylamine, diethylmethylamine, and diisopropylmethylamine.

The order of addition of the base into the polar solvent is arbitrary, but it is preferable to sequentially add an organic base and an asymmetric catalyst into a solution containing racemic carboxylic acids, an alcohol or a phenol derivative, and an acid anhydride.

The amount of each added is not particularly limited, but it is preferable to use an alcohol or a phenol derivative at an amount to be the equivalent or more with respect to the racemic carboxylic acids and it is more preferable to use an alcohol or a phenol derivative at an amount to be from 1.0 to 1.5 equivalent with respect to the racemic carboxylic acids in order to consume the entire racemic carboxylic acids and to convert them into an optically active carboxylic acid ester.

An acid anhydride is required since it forms a mixed acid anhydride with racemic carboxylic acids to be an intermediate which advances the enantioselective esterification, it is preferable to use the acid anhydride at an amount to be the equivalent or more with respect to the racemic carboxylic acids and it is more preferable to use the acid anhydride at an amount to be from 1.0 to 5.0 equivalent with respect to the racemic carboxylic acids.

The base has a function of neutralizing the acid derived from the acid anhydride to be produced in association with the reaction progress and a function of promoting racemization of the mixed acid anhydride to be activated by an asymmetric catalyst. The reaction proceeds even though the base is not added, but it is preferable to add the base at an amount from 1.2 to 4.8 equivalent with respect to the racemic carboxylic acids in order to promote the racemization and to increase the yield and enantiomeric excess of the intended optically active carboxylic acid ester.

An asymmetric catalyst is required in order to advance the enantioselective esterification, and it is preferable to use an asymmetric catalyst at from 0.1 to 10 mol % with respect to the racemic carboxylic acids.

The temperature for reaction is preferably from −23 to 30° C., the time for reaction is preferably from 10 minutes to 72 hours.

EXAMPLES

Hereinafter, Examples of the present invention will be described, but the scope of the present invention is not limited to these Examples.

Incidentally, the following abbreviations are used in Examples in some cases.
Np: naphthyl
Piv2O: pivalic anhydride
Me: methyl
Et: ethyl
n-Pr: n-propyl
i-Pr: isopropyl
n-Bu: n-butyl
i-Bu: isobutyl
n-Hex: n-hexyl
Ac: acetyl
Ph: phenyl
Bn: benzyl
Tr: trityl
Ms: methanesulfonyl
Boc: tert-butoxycarbonyl
DMF: dimethylformamide
DMA: dimethylacetamide
tR: Retention time In the following Examples, (R)-benzo-tetramisole ((R)-BTM) represented by the following formula was used as an asymmetric catalyst.

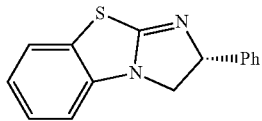 [SMILES: c1ccc([C@@H]2CN3C(=N2)Sc2ccccc23)cc1]

Test Example 1: Effect of α-Nitrogen Substituent of Racemic Carboxylic Acids

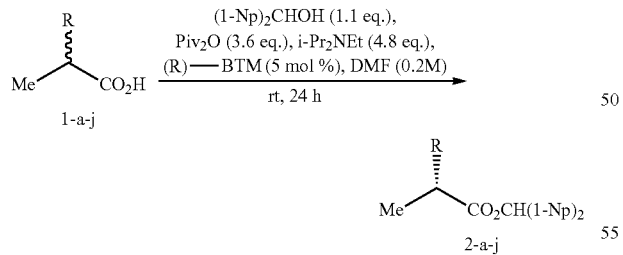

As illustrated in the reaction formula above, the effect of an α-nitrogen substituent on the kinetic resolution by asymmetric esterification of racemic propanoic acids having various α-nitrogen substituents as a base material with di(1-naphthyl)methanol was examined.

Diisopropylethylamine (125 μL, 0.720 μmol) and (R)-BTM (1.9 mg, 75 μmol) were sequentially added to racemic carboxylic acids ((1); 0.150 mol), pivalic anhydride (110 μL, 0.540 mmol), and N,N-dimethylformamide (DMF) containing di(1-naphthyl)methanol (46.9 mg, 0.165 mmol) at room temperature. They were reacted by being stirred for 24 hours at room temperature, and the reaction was then quenched by the addition of saturated ammonium chloride. Thereafter, the mixed solution was extracted with ethyl acetate, the organic layer was separated. The organic layer was dried over sodium sulfate, then filtered, and concentrated under reduced pressure, thereby obtaining a crude product. The optically active ester (2) thus produced and the unreacted optically active carboxylic acid were separated from each other using silica gel thin layer chromatography to obtain the respective compounds. Incidentally, the enantiomeric excess (ee) was determined through HPLC analysis by using a chiral column.

TABLE 1

| Entry | R | Yield of 2/ % | ee of 2/ % |
|---|---|---|---|
| 1 | a (tBu-O-C(O)-NH-*) | 30 | 9.8 |
| 2 | b (phthalimido-*) | 7 | 49 |
| 3 | c (3,3-dimethyl-2-oxoindolin-1-yl, *) | 12 | 32 |
| 4 | d (isatin-N-*) | 36 | 84 |
| 5 | e (benzoxazol-2(3H)-one-3-yl, *) | 80 | 86 |
| 6 | f (2-oxopyrrolidin-1-yl, *) | 47 | 76 |

TABLE 1-continued

| Entry | R | Yield of 2/% | ee of 2/% |
|---|---|---|---|
| 7 | 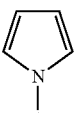 g | 76 | 86 |
| 8 | 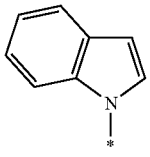 h | 87 | 91 |
| 9 | 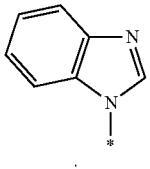 i | 71 | 77 |

As can be seen from Table 1, the reactivity was not sufficient and the yield was 50% or less for all the racemic carboxylic acids having a Boc-protected amino group, an electron-withdrawing imide group, or an amide group as an α-nitrogen substituent (entries 1 to 6). On the other hand, the reaction proceeded with high enantioselectivity and the yield of the corresponding optically active carboxylic acid ester exceeded 50% for all the racemic carboxylic acids having a nitrogen-containing heteroaromatic ring group such as 1H-pyrrol-1-yl group, 1H-indol-1-yl group, a 1H-benzo[d]imidazol-1-yl group, or a 9H-carbazol-9-yl group as an α-nitrogen substituent (entries 7 to 10). In other words, it was apparent that the dynamic kinetic resolution proceeded. Among them, in the case of having a 1H-pyrrol-1-yl group or a 1H-indol-1-yl group, the yield and the enantioselectivity were particularly favorable.

The physical properties of the optically active carboxylic acid esters thus obtained are as follows.

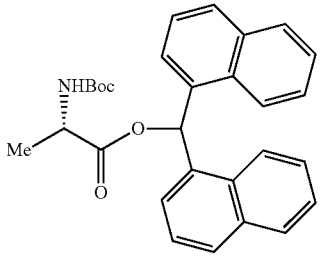 [SMILES: C[C@H](NC(=O)OC(C)(C)C)C(=O)OC(c1cccc2ccccc12)c1cccc2ccccc12]

Di(1-naphthyl)methyl (S)-2-((tert-butoxycarbonyl)amino)propanoate (2a) [in Table 1, Entry 1; 30% Yield, 9.8% ee]

HPLC (CHIRALPAK IA-3, i-PrOH/hexane=1/4, flow rate=0.75 mL/min): tR=17.9 min (54.9%), tR=24.4 min (45.1%);
1H NMR (CDCl3): δ
8.42 (s, 1H, 1'-H),
8.03-7.75 (m, 6H, Ar),
7.57-7.27 (m, 8H, Ar),
5.09 (d, J=7.2 Hz, 1H, NH),
4.46 (td, J=7.2, 7.2 Hz, 1H, 2-H),
1.40 (s, 9H, t-Bu),
1.38 (d, J=7.2 Hz, 3H, 3-CH3);
13C NMR (CDCl3): δ172.6 (1), 155.0 (Boc), 134.4, 134.2, 133.81, 133.79, 131.0, 130.9, 129.18, 129.16, 128.9, 128.8, 126.74, 126.68, 125.9, 125.9, 125.8, 125.23, 125.20, 123.4, 123.2, 123.2, 79.8 (t-Bu), 71.9 (1'), 49.5 (2), 28.3 (t-Bu), 18.7 (3);
HR MS: calcd for C29H29NO4Na (M+Na+) 478.1989, found 478.1970.

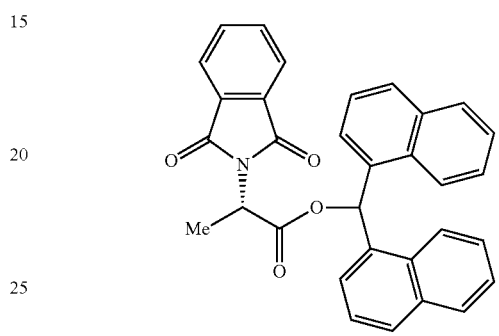

Di(1-naphthyl)methyl (S)-2-(1,3-dioxoisoindolin-2-yl)propanoate (2b) [in Table 1, entry 2; 7% yield, 49% ee]

HPLC (CHIRALPAK ID, i-PrOH/hexane=1/9, flow rate=0.75 mL/min): tR=43.0 min (25.6%), tR=51.9 min (74.4%).

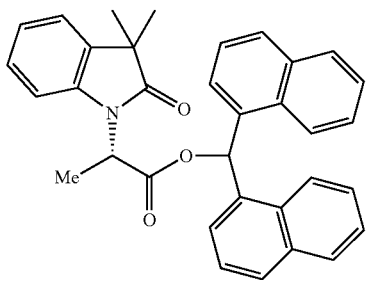 [SMILES: C[C@@H](C(=O)OC(c1cccc2ccccc12)c1cccc2ccccc12)N1C(=O)C(C)(C)c2ccccc21]

Di(1-naphthyl)methyl (S)-2-(3,3-dimethyl-2-oxoindolin-1-yl)propanoate (2c) [in Table 1, Entry 3; 12% Yield, 32% ee]

HPLC (CHIRALPAK AD-H, i-PrOH/hexane=1/19, flow rate=0.75 mL/min): tR=19.3 min (66.1%), tR=21.8 min (33.9%);
1H NMR (CDCl3): δ
8.40 (s, 1H, 1'-H),
7.96-7.67 (m, 6H, Ar),
7.49-7.37 (m, 5H, Ar),
7.27-7.23 (m, 1H, Ar),
7.16-7.04 (m, 3H, Ar),
6.99-6.93 (m, 2H, Ar),
6.72-6.66 (m, 1H, Ar), 5.37 (q, J=7.6 Hz, 1H, 2-H), 1.66 (d, J=7.6 Hz, 3H, 3-CH3), 1.25 (s, 3H, CH3), 1.10 (s, 3H, CH3);

13C NMR (CDCl3): δ180.7, 169.6 (1), 140.0, 135.6, 134.4, 134.0, 133.8, 133.6, 130.84, 130.79, 129.1, 129.0, 128.9, 128.7, 127.3, 126.64, 126.60, 126.1, 125.8, 125.6, 125.5, 125.2, 124.9, 123.3, 123.1, 122.4, 122.3, 109.7, 72.3 (1'), 48.7, 43.7, 24.4 (Me), 24.0 (Me), 14.1 (3);

HR MS: calcd for C34H29NO3Na (M+Na+) 522.2040, found 522.2029.

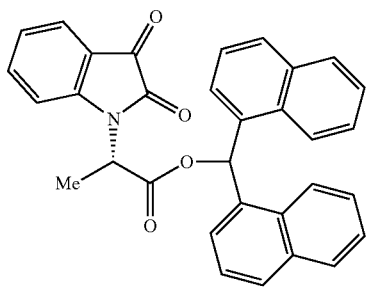 [SMILES: C[C@@H](C(=O)OC(c1cccc2ccccc12)c1cccc2ccccc12)N1C(=O)C(=O)c2ccccc21]

Di(1-naphthyl)methyl (S)-2-(2,3-dioxoindolin-1-yl)propanoate (2d) [in Table 1, Entry 4; 36% Yield, 84% ee]

HPLC (CHIRALCEL OD-H, i-PrOH/hexane=1/9, flow rate=0.75 mL/min): tR=23.2 min (91.9%), tR=30.7 min (8.1%);

1H NMR (CDCl3): δ

8.45 (s, 1H, 1'-H), 8.01-7.70 (m, 6H, Ar), 7.53-7.34 (m, 7H, Ar), 7.26-7.20 (m, 2H, Ar), 7.09 (t, J=8.0 Hz, 1H, Ar), 6.92 (t, J=7.6 Hz, 1H, Ar), 6.51 (d, J=8.0 Hz, 1H, Ar), 5.35 (q, J=7.2 Hz, 1H, 2-H), 1.68 (d, J=7.2 Hz, 3H, 3-CH3);

13 NMR (CDCl3): δ182.3, 168.9 (1), 157.7, 148.9, 137.8, 133.9, 133.8, 133.7, 130.84, 130.81, 129.40, 129.40, 129.37, 129.0, 128.9, 126.7, 126.7, 126.5, 125.9, 125.8, 125.8, 125.3, 125.2, 125.0, 123.6, 123.3, 123.2, 117.6, 111.5, 73.4 (1'), 49.2 (2), 14.2 (3);

HR MS: calcd for C32H23NO4Na (M+Na+) 508.1519, found 508.1526.

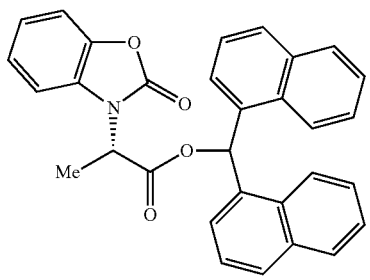 [SMILES: C[C@@H](C(=O)OC(c1cccc2ccccc12)c1cccc2ccccc12)n1c(=O)oc2ccccc21]

Di(1-naphthyl)methyl (S)-2-(2-oxobenzo[d]oxazol-3(2H)-yl)propanoate (2e) [in Table 1, entry 4; 50% yield, 86% ee]

HPLC (CHIRALPAK IC-3, i-PrOH/hexane=1/19, flow rate=0.75 mL/min): tR=46.3 min (7.1%), tR=50.7 min (92.9%);

1H NMR (CDCl3): δ

8.46 (s, 1H, 1'-H), 8.01-7.71 (m, 6H, Ar), 7.54-7.33 (m, 6H, Ar), 7.27-7.09 (m, 3H, Ar), 7.01 (ddd, J=8.0, 7.6, 1.2 Hz, 1H, Ar), 6.87 (ddd, J=8.0, 7.6, 0.8 Hz, 1H, Ar), 6.73 (dd, J=7.6, 1.2 Hz, 1H, Ar), 5.24 (q, J=7.6 Hz, 1H, 2-H), 1.75 (d, J=7.6 Hz, 3H, 3-CH3);

13C NMR (CDCl3): δ168.7 (1), 154.0, 142.5, 133.95, 133.89, 133.8, 133.7, 130.9, 130.8, 129.4, 129.3, 129.2, 129.0, 128.9, 126.8, 126.7, 126.1, 126.0, 125.88, 125.86, 125.2, 125.1, 123.6, 123.2, 123.1, 122.5, 110.1, 109.9, 73.0 (1'), 51.7 (2), 14.9 (3);

HR MS: calcd for C31H23NO4Na (M+Na+) 496.1519, found 496.1496.

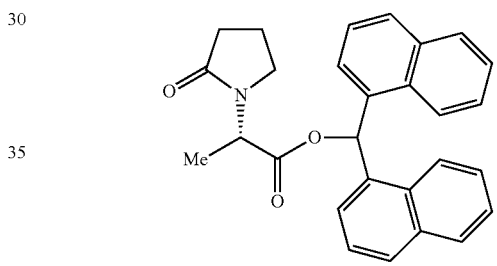

Di(1-naphthyl)methyl (S)-2-(2-oxopyrrolidin-1-yl)propanoate (2f) [in Table 1, Entry 6; 47% Yield, 76% ee]

HPLC (CHIRALPAK AS-H, i-PrOH/hexane=1/9, flow rate=0.75 mL/min): tR=31.2 min (11.9%), tR=43.2 min (88.1%);

1H NMR (CDCl3): δ

8.39 (s, 1H, 1'-H), 8.09-7.78 (m, 6H, Ar), 7.56-7.29 (m, 8H, Ar), 5.04 (q, J=7.2 Hz, 1H, 2-H), 3.36-3.16 (m, 2H, 3'-CH2), 2.38-2.20 (m, 2H, 5'-CH2), 1.93-1.67 (m, 2H, 4'-CH2), 1.42 (d, J=7.2 Hz, 3H, 3-CH3);

13C NMR (CDCl3): δ175.2, 170.8 (1), 134.4, 134.3, 133.8, 133.8, 131.0, 130.9, 129.2, 129.1, 128.9, 128.9, 126.8, 126.6, 126.2, 125.9, 125.8, 125.7, 125.3, 125.2, 123.27, 123.25, 72.0 (1'), 49.5, 43.4, 30.7, 18.0, 14.7 (3);

HR MS: calcd for C28H25NO3Na (M+Na+) 446.1727, found 446.1706.

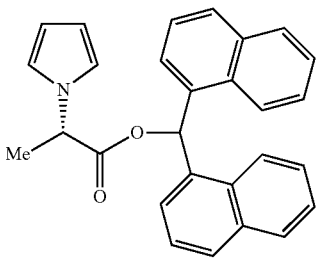 [SMILES: C[C@@H](C(=O)OC(c1cccc2ccccc12)c1cccc2ccccc12)n1cccc1]

Di(1-naphthyl)methyl (S)-2-(1H-pyrrol-1-yl)propanoate (2g) [in Table 1, Entry 7; 76.1% Yield, 86% ee]

1H NMR (CDCl3): δ
8.39 (s, 1H, 1'-H),
8.05-7.72 (m, 6H, Ar),
7.54-7.28 (m, 6H, Ar),
7.15 (d, J=7.2 Hz, 1H, Ar),
7.03 (d, J=7.2 Hz, 1H, Ar),
6.73 (t, J=2.0 Hz, 2H, pyrrole),
6.21 (t, J=2.0 Hz, 2H, pyrrole),
4.86 (q, J=7.2 Hz, 1H, 2-H),
1.73 (d, J=7.2 Hz, 3H, 3-CH3);

13C NMR (CDCl3): δ170.2 (1), 134.2, 134.0, 133.8, 133.7, 131.0, 130.8, 129.2, 129.1, 128.9, 128.8, 126.8, 126.7, 126.1, 125.9, 125.8, 125.5, 125.3, 125.3, 123.2, 123.1, 119.8 (pyrrole), 108.8 (pyrrole), 71.9 (1'), 57.1 (2), 17.8 (3);

HR MS: calcd for C28H23NO2Na (M+Na+) 428.1621, found 428.1603. Incidentally, the enantiomeric excess of Compound 2g was determined after Compound 2g was reduced with LiAlH4, acylated with p-nitrobenzoyl chloride, and converted into the corresponding p-nitrobenzoic acid ester 2g'.

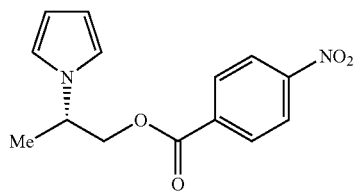 [SMILES: C[C@@H](COC(=O)c1ccc([N+](=O)[O-])cc1)n1cccc1]

(S)-2-(1H-pyrrol-1-yl)propyl 4-nitrobenzoate (2g')

HPLC (CHIRALPAK AD-H, i-PrOH/hexane=1/19, flow rate=0.75 mL/min): tR=19.6 min (92.8%), tR=22.0 min (7.2%);
1H NMR (CDCl3): δ
8.32-8.22 (m, 2H, Ar),
8.18-8.06 (m, 2H, Ar),
6.77 (t, J=2.0 Hz, 2H, pyrrole),
6.18 (t, J=2.0 Hz, 2H, pyrrole),
4.59-4.40 (m, 3H, 2-H, 1-CH2),
1.61 (d, J=6.4 Hz, 3H, 3-CH3);
13C NMR (CDCl3): δ164.2, 150.6, 135.0, 130.7, 123.6, 118.8 (pyrrole), 108.4 (pyrrole), 69.1 (1), 53.5 (2), 17.7 (3);
HR MS: calcd for C14H14N2O4Na (M+Na+) 297.0846, found 297.0844.

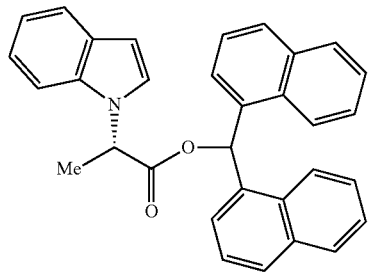 [SMILES: C[C@@H](C(=O)OC(c1cccc2ccccc12)c1cccc2ccccc12)n1ccc2ccccc21]

Di(1-naphthyl)(S)-methyl 2-(1H-indol-1-yl)propanoate (2h) [In Table 1, Entry 8; 87% Yield, 91% ee]

1H NMR (CDCl3): δ
8.37 (s, 1H, 1'-H),
7.93-7.72 (m, 6H, Ar),
7.67-7.60 (m, 1H, Ar),
7.50-7.33 (m, 4H, Ar),
7.26-7.00 (m, 7H, Ar),
6.98-6.88 (m, 1H, Ar),
6.52 (d, J=3.2 Hz, 1H, Ar),
5.22 (q, J=7.2 Hz, 1H, 2-H),
1.81 (d, J=7.2 Hz, 3H, 3-CH3);

13C NMR (CDCl3): δ170.5 (1), 136.2, 134.0, 133.9, 133.73, 133.72, 130.90, 130.87, 129.1, 129.1, 128.9, 128.84, 128.76, 126.69, 126.66, 125.9, 125.84, 125.84, 125.81, 125.2, 125.1, 125.0, 123.2, 123.1, 121.8, 121.0, 120.0, 109.4, 102.5, 72.1 (1'), 53.9 (2), 17.0 (3);

HR MS: calcd for C32H25NO2Na (M+Na+) 478.1778, found 478.1774.

Incidentally, the enantiomeric excess of Compound 2h was determined after Compound 2h was reduced with LiAlH4 and converted into the corresponding alcohol 2h'.

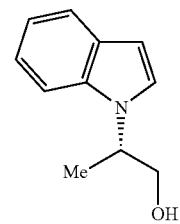 [SMILES: C[C@@H](CO)n1ccc2ccccc21]

(S)-2-(1H-Indol-1-yl)propan-1-ol (2h')

HPLC (CHIRALCEL OJ-H, i-PrOH/hexane=1/9, flow rate=0.75 mL/min): tR=28.4 min (4.7%), tR=33.5 min (95.3%);
1H NMR (CDCl3): δ
7.64 (d, J=8.4 Hz, 1H, Ar),
7.41 (d, J=8.4 Hz, 1H, Ar),
7.30-7.17 (m, 2H, Ar),
7.11 (ddd, J=8.0, 7.6, 0.8 Hz, 1H, Ar),
6.57 (d, J=0.8 Hz, 1H, Ar),
4.67 (tdd, J=6.8, 6.4, 5.2 Hz, 1H, 2-H),
3.90 (dd, J=11.6, 6.4 Hz, 1H, 1-CH2),
3.87 (dd, J=11.6, 5.2 Hz, 1H, 1-CH2),
1.56 (d, J=6.8 Hz, 3H, 3-CH3),
1.48 (br m, 1H, OH);

13C NMR (CDCl3): δ136.2, 128.6, 124.2, 121.5, 121.0, 119.6, 109.5, 102.0, 66.4 (1), 53.1 (2), 16.9 (3);
HR MS: calcd for C11H14NO (M+H+) 175.1070, found 175.1062.

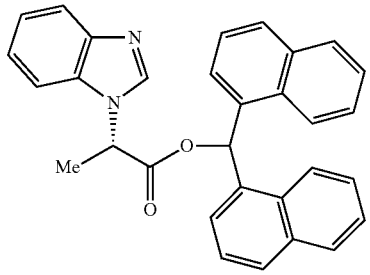 [SMILES: C[C@@H](C(=O)OC(c1cccc2ccccc12)c1cccc2ccccc12)n1cnc2ccccc21]

Di(1-naphthyl)methyl (S)-2-(1H-benzo[d]imidazol-1-yl)propanoate (2i) [in Table 1, entry 9; 71% yield, 77% ee]

HPLC (CHIRALPAK ID, i-PrOH/hexane=2/3, flow rate=0.5 mL/min): tR=29.6 min (11.3%), tR=35.9 min (88.7%);
1H NMR (CDCl3): δ
8.41 (s, 1H, 1'-H),
7.97 (s, 1H, benzimidazole-2'),
7.92-7.72 (m, 7H, Ar),
7.51-7.32 (m, 4H, Ar),
7.30-7.07 (m, 6H, Ar),
6.98 (d, J=7.2 Hz, 1H, Ar),
5.18 (q, J=7.2 Hz, 1H, 2-H),
1.87 (d, J=7.2 Hz, 3H, 3-CH3);
13C NMR (CDCl3): δ169.3 (1), 143.7, 141.2, 141.2, 133.78, 133.76, 133.7, 133.5, 133.4, 130.82, 130.80, 129.34, 129.31, 128.9, 128.9, 126.7, 125.93, 125.93, 125.91, 125.8, 125.10, 125.07, 123.1, 123.0, 122.9, 122.5, 120.5, 109.9, 72.8 (1'), 53.8 (2), 17.0 (3);
HR MS: calcd for C31H25N2O2 (M+H+) 457.1911, found 457.1911.

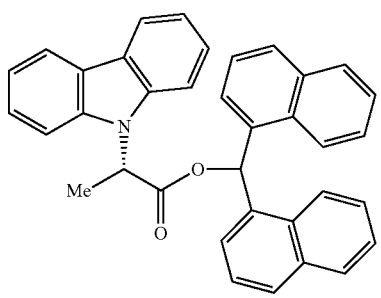 [SMILES: C[C@@H](C(=O)OC(c1cccc2ccccc12)c1cccc2ccccc12)n1c2ccccc2c2ccccc21]

Di(1-naphthyl)methyl (S)-2-(9H-carbazol-9-yl)propanoate (2j) [in Table 1, entry 10; 62% yield, 64% ee]

1H NMR (CDCl3): δ
8.48 (s, 1H, 1'-H),
8.21-8.02 (m, 3H, Ar),
7.92-7.70 (m, 4H, Ar),
7.64 (d, J=8.0 Hz, 1H, Ar),
7.56-7.45 (m, 2H, Ar),
7.41-7.06 (m, 10H, Ar),
6.91 (t, J=7.8 Hz, 1H, Ar),
6.75 (d, J=6.8 Hz, 1H, Ar),
5.47 (q, J=7.2 Hz, 1H, 2-H),
1.84 (d, J=7.2 Hz, 3H, 3-CH3);
13C NMR (CDCl3): δ170.2 (1), 139.6, 134.4, 133.9, 133.8, 133.6, 131.1, 130.6, 129.3, 129.0, 128.73, 128.67, 126.9, 126.6, 126.4, 125.9, 125.7, 125.6, 125.5, 125.2, 124.9, 123.5, 123.3, 123.2, 120.2, 119.4, 109.6, 72.3 (1'), 52.4 (2), 15.4 (3);
HR MS: calcd for C36H27NO2Na (M+Na+) 528.1934, found 528.1942. Incidentally, the enantiomeric excess of Compound 2j was determined after Compound 2j was reduced with LiAlH4 and converted into the corresponding alcohol 2j'.

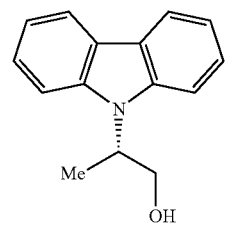 [SMILES: C[C@@H](CO)n1c2ccccc2c2ccccc21]

(S)-2-(9H-Carbazol-9-yl)propan-1-ol (2j')

HPLC (CHIRALCEL OD-H, i-PrOH/hexane=1/9, flow rate=1.0 mL/min): tR=24.2 min (18.0%), tR=35.0 min (82.0%);
1H NMR (CDCl3): δ
8.09 (d, J=7.6 Hz, 2H, Ar),
7.55-7.37 (m, 4H, Ar),
7.27-7.17 (m, 2H, Ar),
4.89 (dtd, J=9.2, 7.6, 4.8 Hz, 1H, 2-H),
4.26 (dd, J=11.2, 9.2 Hz, 1H, 1-CH2),
3.91 (dd, J=11.2, 4.8 Hz, 1H, 1-CH2),
1.64 (d, J=7.6 Hz, 3H, 3-CH3),
1.79-1.38 (br m, 1H, OH);
13C NMR (CDCl3): δ139.9, 125.6, 123.5, 120.3, 119.1, 110.0, 64.5 (1), 53.4 (2), 15.1 (3);
HR MS: calcd for C15H15NONa (M+Na+) 248.1046, found 248.1052.

Test Example 2: Effect of Reaction Solvent

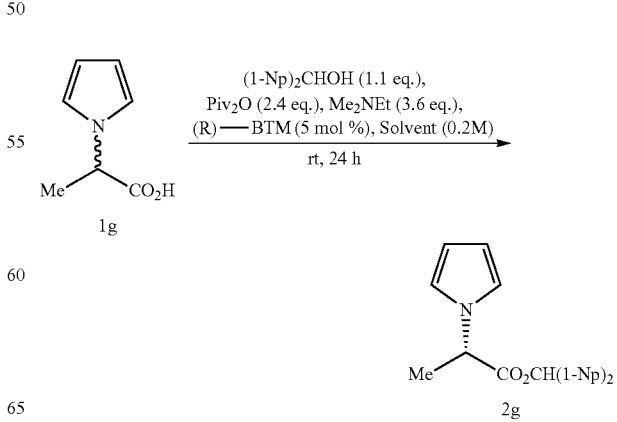

As illustrated in the reaction formula above, the effect of a reaction solvent on kinetic resolution by asymmetric esterification of racemic carboxylic acids (1 g) as a base material with di(1-naphthyl)methanol was examined. Incidentally, the reaction conditions were the same as those in Test Example 1 described above except that the amounts of dimethylethylamine as a base material, pivalic anhydride, and di(1-naphthyl)methanol used were those in the reaction formula above and the reaction solvent was as presented in the following Table 2.

TABLE 2

| Entry | Reaction solvent | Dipole moment of reaction solvent/D | Yield of 2 g/% | ee of 2 g/% | E |
|---|---|---|---|---|---|
| 1 | Toluene | 0.37 | 91 | 42 | 76.4 |
| 2 | Diethyl ether | 1.12 | 58 | 87 | 101.0 |
| 3 | Dichloromethane | 1.14 | 68 | 85 | 115.6 |
| 4 | Tetrahydrofuran | 1.70 | 87 | 65 | 113.1 |
| 5 | Ethyl acetate | 1.88 | 77 | 59 | 90.9 |
| 6 | Acetone | 2.69 | 77 | 65 | 100.1 |
| 7 | Acetonitrile | 3.44 | 89 | 66 | 117.5 |
| 8 | Dimethylacetamide | 3.72 | 99 | 91 | 180.2 |
| 9 | Dimethylformamide | 3.86 | 72 | 87 | 125.3 |
| 10 | 1,3-dimethyl-2-imidazolidinone | 4.07 | 82 | 91 | 149.2 |
| 11 | N-methylpyrrolidone | 4.09 | 84 | 92 | 154.6 |
| 12 | Dimethyl sulfoxide | 4.30 | 88 | 90 | 158.4 |

In the table, the E value is an indicator which indicates the efficiency of optical resolution, and it is defined as E (%)=yield (%)×ee (%)×2÷ 100. The theoretical upper limit value of the E value in the dynamic kinetic resolution is 200, and the fact that the E value is 200 means that the optically pure intended product is obtained from the racemic base material at 100% yield.

As can be seen from Table 2, in the case of using a polar solvent having a dipole moment of 3.5 or more, the E value was from 125.3 to 180.2 and the reaction proceeded with favorable efficiency (entries 8 to 12). On the other hand, in the case of using a polar solvent having a dipole moment of less than 3.5, the E value was only from 76.4 to 117.5 as a result of a great decrease in enantioselectivity (entries 1 to 7).

Test Example 3: Effect of Base

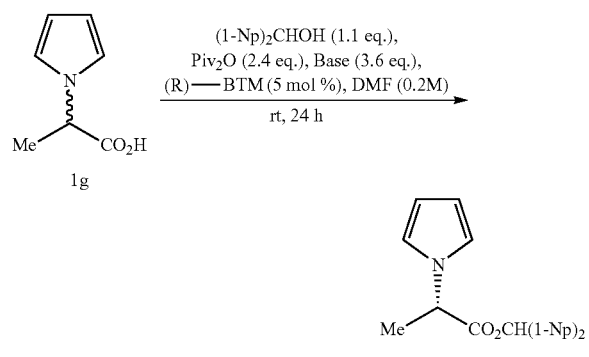

As illustrated in the reaction formula above, the effect of a base on the dynamic kinetic resolution by asymmetric esterification was examined. Incidentally, the reaction conditions are the same as those in Test Example 2 described above.

TABLE 3

| Entry | Base | Yield of 2 g/% | ee of 2 g/% | E |
|---|---|---|---|---|
| 1 | None | 85 | 17 | 28.9 |
| 2 | N,N-dimethyl aniline | 58 | 15 | 17.4 |
| 3 | Pyridine | 77 | 17 | 26.2 |
| 4 | Triethylamine | 76 | 88 | 133.8 |
| 5 | Diisopropylethylamine | 75 | 86 | 129.0 |
| 6 | Diazabicycloundecene | 42 | 2 | 1.7 |
| 7 | N-methylpiperidine | 50 | 91 | 91.0 |
| 8 | N-methylpyrrolidine | 50 | 90 | 90.0 |
| 9 | 1,2,2,6,6-pentamethylpiperidine | 38 | 89 | 67.6 |
| 10 | Dimethylethylamine | 78 | 91 | 142.0 |
| 11 | Dimethylisopropylamine | 68 | 89 | 121.0 |
| 12 | Diethylmethylamine | 63 | 92 | 115.9 |
| 13 | Diisopropylmethylamine | 68 | 88 | 119.7 |

As can be seen from Table 3, the efficiency of the reaction was low when those that exhibited low basicity and/or high ability to promote acylation or a cyclic amine were used as a base (entries 2, 3, and 6 to 9). On the other hand, the efficiency of the reaction was favorable when an amine which was represented by the general formula (i) and had only an alkyl group was used as a base (entries 4, 5, and 10 to 13).

Test Example 4: Effect of Combination of Reaction Solvent with Base

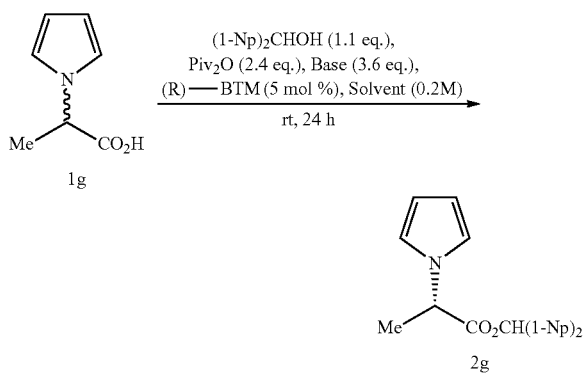

As illustrated in the reaction formula above, the effect of the combination of dimethylformamide or dimethylacetamide which provided favorable results on the examination of the solvent in Test Example 2 with diisopropylethylamine, triethylamine, diethylmethylamine, and dimethylethylamine which provided favorable results on the examination of the base in Test Example 3 on the dynamic kinetic resolution by asymmetric esterification were examined. Incidentally, the reaction conditions are the same as those in Test Example 2 described above.

TABLE 4

| Entry | Base | Reaction solvent | Yield of 2 g/% | ee of 2 g/% | E |
|---|---|---|---|---|---|
| 1 | Diisopropylethylamine | Dimethylformamide | 75 | 86 | 129.0 |

TABLE 4-continued

| Entry | Base | Reaction solvent | Yield of 2 g/% | ee of 2 g/% | E |
|---|---|---|---|---|---|
| 2 | Diisopropylethyl-amine | Dimethylacetamide | 99 | 91 | 180.2 |
| 3 | Triethylamine | Dimethylformamide | 76 | 88 | 133.8 |
| 4 | Triethylamine | Dimethylacetamide | 84 | 93 | 156.2 |
| 5 | Diethylmethylamine | Dimethylformamide | 63 | 92 | 115.9 |
| 6 | Diethylethylamine | Dimethylacetamide | 78 | 88 | 137.3 |
| 7 | Dimethylethylamine | Dimethylformamide | 78 | 91 | 142.0 |
| 8 | Dimethylethylamine | Dimethylacetamide | 88 | 96 | 169.0 |

As can be seen from Table 4, the reaction proceeded with favorable efficiency in any combination of a base selected from diisopropylethylamine, triethylamine, diethylmethylamine, or dimethylethylamine with a reaction solvent selected from dimethylformamide or dimethylacetamide, and the E value was from 115.9 to 180.2.

Test Example 5: Effect of Substituent on Nitrogen-Containing Heterocyclic Aromatic Ring of Base Material

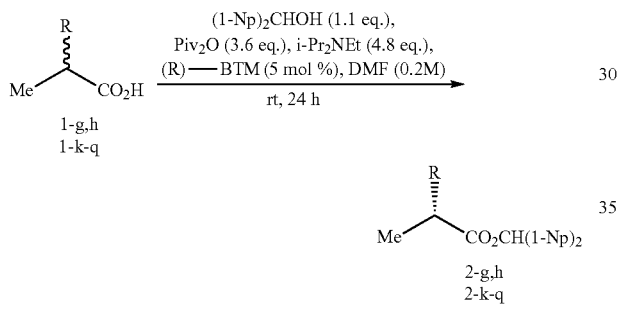

As illustrated in the reaction formula above, the effect of a substituent on the nitrogen-containing heterocyclic aromatic ring of the base material on dynamic kinetic resolution by asymmetric esterification was examined. Incidentally, the reaction conditions are the same as those in Test Example 1 described above.

TABLE 5

| Entry | R | Yield of 2/% | ee of 2/% |
|---|---|---|---|
| 1 | g (pyrrole) | 78 | 86 |
| 2 | h (indole) | 87 | 91 |
| 3 | k (Ac-pyrrole) | 56 | 94 |
| 4 | l (NC-pyrrole) | 73 | 88 |
| 5 | m (Ph-pyrrole) | 67 | 82 |
| 6 | n (Ac-pyrrole) | 80 | 75 |
| 7 | o (Cl-indole) | 92 | 85 |
| 8 | p (MeO-indole) | 90 | 80 |
| 9 | q (Ac-indole) | 78 | 84 |

As can be seen from Table 5, it was possible to obtain an optically active carboxylic acid ester at a high yield and with high enantioselectivity even in the case of using any base material regardless of the electronic effect and position of the substituent on the nitrogen-containing heteroaromatic ring of the base material, but particularly favorable results were obtained in the case of there being no substitution (entries 1 to 9).

The physical properties of the optically active carboxylic acid esters thus obtained are as follows.

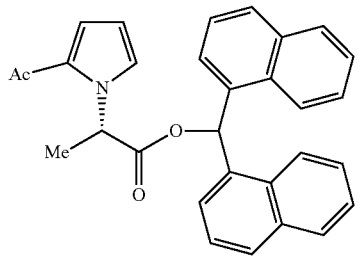

Di(1-naphthyl)methyl (S)-2-(2-acetyl-1H-pyrrol-1-yl)propanoate (2k) [in Table 5, Entry 3; 56% Yield, 94% ee]

HPLC (CHIRALPAK AD-H, i-PrOH/hexane=1/9, flow rate=1.0 mL/min): tR=13.4 min (96.9%), tR=22.5 min (3.1%);
1H NMR (CDCl3): δ
8.37 (s, 1H, 1'-H),
8.02 (d, J=5.6 Hz, 1H, Ar),
7.98-7.73 (m, 5H, Ar),
7.58-7.18 (m, 8H, Ar),
7.09-7.00 (m, 1H, Ar),
6.98-6.89 (m, 1H, Ar),
6.26-6.09 (br m, 2H, pyrrole, 2-H),
2.28 (s, 3H, Ac-CH3),
1.66 (d, J=7.2 Hz, 3H, 3-CH3);
13C NMR (CDCl3): δ188.5 (Ac), 170.8 (1), 134.6, 134.2, 133.9, 133.8, 131.1, 130.9, 130.6, 129.2, 129.0, 128.8, 128.7, 127.0, 126.7, 126.6, 126.2, 125.9, 125.84, 125.75, 125.2, 125.2, 123.7, 123.4, 120.5, 108.7, 72.3 (1'), 55.7 (2), 27.1 (Ac), 17.7 (3);
HR MS: calcd for C30H25NO3Na (M+Na+) 470.1727, found 470.1726.

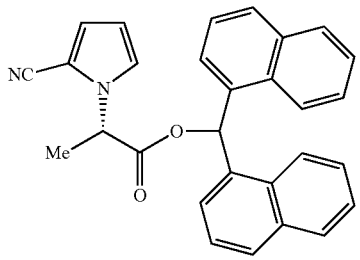 [SMILES: CC(=O)c1cccn1[C@@H](C)C(=O)OC(c1cccc2ccccc12)c1cccc2ccccc12]

Di(1-naphthyl)methyl (S)-2-(2-cyano-1H-pyrrol-1-yl)propanoate (2l) [in Table 5, Entry 4; 73% Yield, 88% ee]

HPLC (CHIRALPAK IC-3, i-PrOH/hexane=1/19, flow rate=0.75 mL/min): tR=18.6 min (5.9%), tR=21.5 min (94.1%);
1H NMR (CDCl3): δ
8.41 (s, 1H, 1'-H),
8.05-7.78 (m, 6H, Ar),
7.56-7.30 (m, 8H, Ar),
6.94 (dd, J=2.8, 1.6 Hz, 1H, pyrrole),
6.79 (dd, J=4.0, 1.6 Hz, 1H, pyrrole),
6.18 (dd, J=4.0, 2.8 Hz, 1H, pyrrole),
5.18 (q, J=7.2 Hz, 1H, 2-H),
1.77 (d, J=7.2 Hz, 3H, 3-CH3);
13C NMR (CDCl3): δ169.2 (1), 133.9, 133.84, 133.76, 133.6, 131.0, 130.8, 129.5, 129.3, 129.0, 128.9, 126.9, 126.9, 126.2, 126.0, 125.9, 125.7, 125.24, 125.20, 124.5, 123.1, 123.0, 120.4, 113.3, 110.2, 104.4, 73.0 (1'), 56.0 (2), 18.0 (3);
HR MS: calcd for C29H22N2O2Na (M+Na+) 453.1573, found 453.1571.

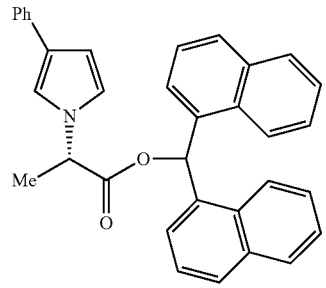 [SMILES: C[C@@H](C(=O)OC(c1cccc2ccccc12)c1cccc2ccccc12)n1ccc(-c2ccccc2)c1]

Di(1-naphthyl)methyl (S)-2-(3-phenyl-1H-pyrrol-1-yl)propanoate (2m) [in Table 5, Entry 5; 67% Yield, 82% ee]

1H NMR (CDCl3): δ
8.33 (s, 1H, 1'-H),
7.94-7.87 (m, 1H, Ar),
7.83-7.66 (m, 5H, Ar),
7.44-7.05 (m, 12H, Ar),
6.97 (d, J=7.2 Hz, 1H, Ar),
6.91 (dd, J=2.4, 2.0 Hz, 1H, pyrrole),
6.65 (dd, J=2.8, 2.4 Hz, 1H, pyrrole),
6.42 (dd, J=2.8, 2.0 Hz, 1H, pyrrole),
4.75 (q, J=7.2 Hz, 1H, 2-H),
1.66 (d, J=7.2 Hz, 3H, 3-CH3);
13C NMR (CDCl3): δ170.0 (1), 135.7, 134.1, 134.0, 133.8, 133.7, 131.0, 130.8, 129.3, 129.1, 128.9, 128.8, 128.5, 128.5, 126.8, 126.7, 126.2, 125.9, 125.8, 125.6, 125.50, 125.47, 125.3, 125.1, 123.13, 123.10, 120.9, 116.5, 107.0, 72.1 (1'), 57.3 (2), 17.7 (3);
HR MS: calcd for C34H27NO2Na (M+Na+) 504.1934, found 504.1948.

Incidentally, the enantiomeric excess of Compound 2m was determined after Compound 2m was reduced with LiAlH4 and converted into the corresponding alcohol 2m'.

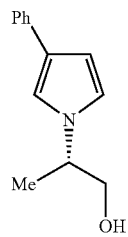

(S)-2-(3-Phenyl-1H-pyrrol-1-yl)propan-1-ol (2m')

HPLC (CHIRALPAK AD-H, i-PrOH/hexane=1/9, flow rate=0.75 mL/min): tR=10.0 min (91.0%), tR=11.5 min (9.0%);

1H NMR (C6D6): δ
7.64-7.53 (m, 2H, Ar),
7.34-7.21 (m, 2H, Ar),
7.14-7.06 (m, 1H, Ar),
6.80 (dd, J=2.2, 1.8 Hz, 1H, pyrrole),
6.57 (dd, J=2.6, 1.8 Hz, 1H, pyrrole),
6.42 (dd, J=2.6, 2.2 Hz, 1H, pyrrole),
3.56-3.41 (m, 1H, 2-H),
3.23-3.08 (m, 2H, 1-CH2),
1.16-1.00 (br m, 1H, OH),
0.93 (d, J=6.9 Hz, 3H, 3-CH3);

13C NMR (C6D6): δ136.8, 129.0, 128.7, 125.6, 125.4, 120.1, 115.9, 106.7, 67.2 (1), 57.2 (2), 17.1 (3);

HR MS: calcd for C13H15NONa (M+Na+) 224.1046, found 224.1040.

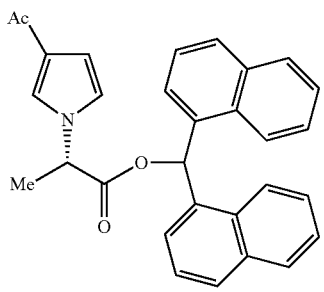 [SMILES: CC(=O)c1ccn([C@@H](C)C(=O)OC(c2cccc3ccccc23)c2cccc3ccccc23)c1]

Di(1-naphthyl)methyl (S)-2-(3-acetyl-1H-pyrrol-1-yl)propanoate (2n) [in Table 5, Entry 6; 80% Yield, 75% ee]

HPLC (CHIRALPAK IC-3, i-PrOH/hexane=3/7, flow rate=0.4 mL/min): tR=36.9 min (12.6%), tR=46.4 min (87.4%);

1H NMR (CDCl3): δ
8.41 (s, 1H, 1'-H),
7.99-7.76 (m, 6H, Ar),
7.55-7.26 (m, 6H, Ar),
7.26-7.17 (m, 2H, Ar),
7.09 (d, J=7.2 Hz, 1H, Ar),
6.66 (dd, J=2.8, 2.4 Hz, 1H, pyrrole),
6.61 (dd, J=2.8, 1.6 Hz, 1H, pyrrole),
4.81 (q, J=7.2 Hz, 1H, 2-H),
2.31 (s, 3H, Ac-CH3),
1.73 (d, J=7.2 Hz, 3H, 3-CH3);

13C NMR (CDCl3): δ193.3 (Ac), 169.3 (1), 133.77, 133.76, 133.73, 133.67, 130.9, 130.8, 129.4, 129.3, 129.0, 128.9, 126.84, 126.76, 126.4, 126.0, 126.0, 125.9, 125.5, 125.2, 125.1, 124.8, 122.94, 122.93, 121.6, 109.4, 72.5 (1'), 57.6 (2), 27.0 (Ac), 17.8 (3);

HR MS: calcd for C30H25NO3Na (M+Na+) 470.1727, found 470.1707.

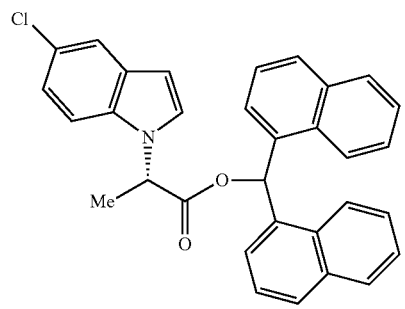 [SMILES: C[C@@H](C(=O)OC(c1cccc2ccccc12)c1cccc2ccccc12)n1ccc2cc(Cl)ccc21]

Di(1-naphthyl)(S)-methyl 2-(5-chloro-1H-indol-1-yl)propanoate (2o) [in Table 5, Entry 7; 92% Yield, 85% ee]

HPLC (CHIRALCEL OD-H, i-PrOH/hexane=1/4, flow rate=0.75 mL/min): tR=9.6 min (7.5%), tR=16.2 min (92.5%);

1H NMR (CDCl3): δ
8.35 (s, 1H, 1'-H),
7.93-7.72 (m, 6H, Ar),
7.57 (d, J=1.6 Hz, 1H, Ar),
7.49-7.31 (m, 4H, Ar),
7.28-7.14 (m, 3H, Ar),
7.07-6.91 (m, 4H, Ar),
6.44 (d, J=3.2 Hz, 1H, indole-3'-H),
5.14 (q, J=7.2 Hz, 1H, 2-H),
1.80 (d, J=7.2 Hz, 3H, 3-CH3);

13C NMR (CDCl3): δ170.1 (1), 134.6, 133.9, 133.84, 133.78, 130.91, 130.87, 129.8, 129.24, 129.22, 128.90, 128.89, 126.71, 126.69, 126.4, 125.93, 125.89, 125.89, 125.8, 125.8, 125.7, 125.11, 125.07, 123.13, 123.06, 122.1, 120.4, 110.4, 102.2, 72.4 (1'), 54.2 (2), 16.9 (3);

HR MS: calcd for C32H24ClNO2Na (M+Na+) 512.1388, found 512.1371.

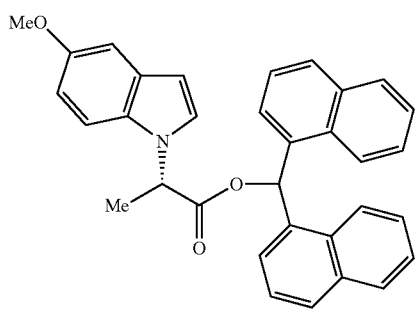 [SMILES: COc1ccc2c(ccn2[C@@H](C)C(=O)OC(c2cccc3ccccc23)c2cccc3ccccc23)c1]

Di(1-naphthyl)methyl (S)-2-(5-methoxy-1H-indol-1-yl)propanoate (2p) [in Table 5, Entry 8; 90% Yield, 80% ee]

HPLC (CHIRALCEL OD-H, i-PrOH/hexane=1/4, flow rate=0.75 mL/min): tR=12.4 min (9.8%), tR=30.8 min (90.2%);

1H NMR (CDCl3): δ
8.36 (s, 1H, 1'-H),
7.94-7.69 (m, 6H, Ar),
7.50-7.30 (m, 4H, Ar),
7.27-6.93 (m, 7H, Ar), 6.74 (dd, J=9.2, 2.8 Hz, 1H, indole-6'-H),
6.44 (d, J=3.2 Hz, 1H, indole-3'-H),
5.14 (q, J=7.2 Hz, 1H, 2-H),
3.84 (s, 3H, indole-5'-OCH3),
1.79 (d, J=7.2 Hz, 3H, 3-CH3);

13C NMR (CDCl3): δ170.5 (1), 154.4, 134.1, 134.0, 133.8, 133.7, 131.6, 130.93, 130.91, 129.2, 129.1, 129.1, 128.9, 128.8, 126.68, 126.66, 125.9, 125.8, 125.8, 125.8, 125.6, 125.15, 125.11, 123.18, 123.16, 112.0, 110.1, 102.9, 102.1, 72.2 (1'), 55.9 (5'-OCH3), 54.1 (2), 16.9 (3);

HR MS: calcd for C33H27NO3Na (M+Na+) 508.1883, found 508.1872.

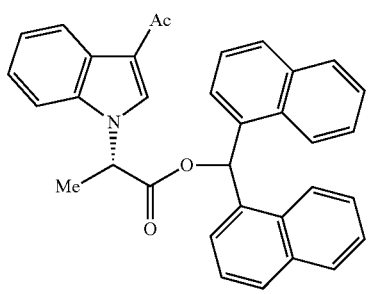 [SMILES: CC(=O)c1cn([C@@H](C)C(=O)OC(c2cccc3ccccc23)c2cccc3ccccc23)c2ccccc12]

Di(1-naphthyl)methyl (S)-2-(3-acetyl-1H-indol-1-yl) propanoate (2q) [in Table 5, Entry 9; 78% Yield, 84% ee]

HPLC (CHIRALCEL OD-H, i-PrOH/hexane=3/7, flow rate=0.75 mL/min): tR=12.0 min (92.1%), tR=18.8 min (7.9%);
1H NMR (CDCl3): δ
8.41 (d, J=8.0 Hz, 1H, indole-2''-H),
8.39 (s, 1H, 1'-H),
7.92-7.74 (m, 7H, Ar),
7.52-7.33 (m, 4H, Ar),
7.33-7.13 (m, 5H, Ar),
7.09 (d, J=7.2 Hz, 1H, Ar),
7.02 (d, J=7.2 Hz, 1H, Ar),
5.25 (q, J=7.2 Hz, 1H, 2-H),
2.38 (s, 3H, Ac-CH3),
1.87 (d, J=7.2 Hz, 3H, 3-CH3);

13C NMR (CDCl3): δ193.1 (Ac), 169.5 (1), 136.8, 133.8, 133.8, 133.6, 133.5, 132.1, 130.83, 130.78, 129.4, 129.3, 128.9, 128.9, 126.79, 126.76, 126.2, 125.98, 125.96, 125.96, 125.8, 125.11, 125.09, 123.6, 123.0, 123.0, 123.0, 122.8, 118.0, 109.5, 72.9 (1'), 54.2 (2), 27.5 (Ac), 17.1 (3);

HR MS: calcd for C34H27NO3Na (M+Na+) 520.1883, found 520.1864.

Test Example 6: Examination of Generality of Base Material

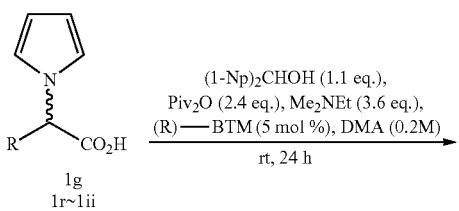

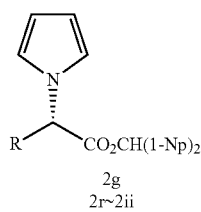

As illustrated in the reaction formula above, the generality of the base material on dynamic kinetic resolution by asymmetric esterification was examined. Incidentally, the reaction conditions are the same as those in Test Example 2 described above. The racemic optically active carboxylic acids were synthesized from the corresponding α-amino acid by the Clauson-Kaas synthesis method.

TABLE 6

| Entry | R | | Yield of 2/ % | ee of 2/ % | E |
|---|---|---|---|---|---|
| 1 | Me | g | 88 | 96 | 169.0 |
| 2 | Et | r | 80 | 75 | 120.0 |
| 3 | n-Pr | t | 89 | 74 | 131,7 |
| 4 | i-Pr | aa | 38 | 91 | 69.2 |
| 5 | n-Bu | bb | Quantitative | 79 | 158.0 |
| 6 | i-Bu | cc | 90 | 74 | 133.2 |
| 7 | n-Hex | dd | Quantitative | 79 | 158.0 |
| 8 | BnO~* | y | 79 | 64 | 101.1 |
| 9 | ⟶=* (allyl) | z | 93 | 85 | 158.1 |
| 10 | ⟶≡* (propargyl) | ee | Quantitative | 94 | 188.0 |
| 11 | Ph-CH2* | s | 88 | 87 | 153.1 |
| 12 | Ph-CH2CH2* | ff | 81 | 65 | 105.3 |
| 13 | 4-MeO-C6H4-CH2* | w | 61 | 88 | 107.4 |
| 14 | 3,4-(MeO)2-C6H3-CH2* | x | 97 | 83 | 161.0 |
| 15 | 1-Naphthyl-CH2* | gg | 76 | 86 | 130.7 |
| 16 | 3-Thienyl-CH2* | hh | 97 | 96 | 186.2 |

TABLE 6-continued

| Entry | R | Yield of 2/ % | ee of 2/ % | E |
|---|---|---|---|---|
| 17 | 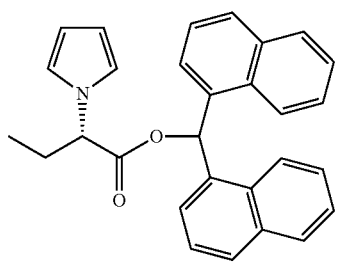 ii (1-methylimidazol-4-yl)methyl | 68 | 65 | 88.4 |
| 18 | (1H-indol-3-yl)methyl u | 59 | 84 | 99.1 |
| 19 | (N-Boc-indol-3-yl)methyl v | 93 | 89 | 165.5 |

As can be seen from Table 6, it was possible to obtain an optically active carboxylic acid ester at a high yield and with high enantioselectivity even in the case of using any base material (entries 1 to 19).

The physical properties of the optically active carboxylic acid esters thus obtained are as follows.

Di(1-naphthyl)methyl (S)-2-(1H-pyrrol-1-yl)propanoate (2g) [in Table 6, Entry 1; 88% Yield, 96% ee]

HPLC (CHIRALPAK OD-H×2, i-PrOH/hexane=1/9, flow rate=0.5 mL/min): tR=26.4 min (1.9%), tR=28.1 min (98.1%)

Other equipment data were consistent with those in Test Example 1.

Di(1-naphthyl)methyl (S)-2-(1H-pyrrol-1-yl)butanoate (2r) [in Table 6, Entry 2; 80% Yield, 75% ee]

HPLC (CHIRALPAK OD-H×2, i-PrOH/hexane=1/9, flow rate=0.5 mL/min): tR=22.4 min (87.6%), tR=24.21 min (12.4%);

1H NMR (CDCl3): δ
8.40 (s, 1H, 1'-H),
8.04-7.71 (m, 6H, Ar),
7.53-7.00 (m, 8H, Ar),
6.76-6.63 (m, 2H, pyrrole),
6.26-6.14 (m, 2H, pyrrole),
4.46 (dd, J=9.2, 6.6 Hz, 1H, 2-H),
2.26-1.92 (m, 2H, 3-CH2),
0.84 (t, J=7.2 Hz, 3H, 4-CH3);

13C NMR (CDCl3): δ169.7 (1), 134.3, 134.1, 133.8, 133.7, 131.0, 130.9, 129.2, 129.0, 128.9, 128.8, 126.7, 126.6, 126.0, 125.9, 125.8, 125.6, 125.2, 125.2, 123.2, 123.1, 120.0 (pyrrole), 108.7 (pyrrole), 71.9 (1'), 63.6 (2), 25.5 (3), 10.3 (4);

HR MS: calcd for C29H25NO2Na (M+Na+) 442.1778, found 442.1757.

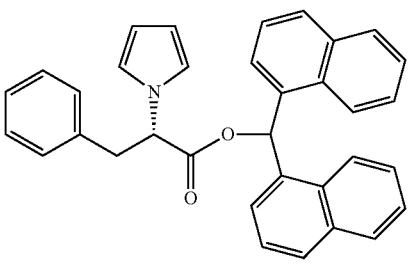 [SMILES: O=C(OC(c1cccc2ccccc12)c1cccc2ccccc12)[C@H](Cc1ccccc1)n1cccc1]

Di(1-naphthyl)methyl (S)-3-phenyl-2-(1H-pyrrol-1-yl)propanoate (2s) [in Table 6, Entry 11; 88% Yield, 87% ee]

1H NMR (CDCl3): δ
8.33 (s, 1H, 1'-H),
7.98-7.64 (m, 6H, Ar),
7.56-7.11 (m, 9H, Ar),
7.10-6.90 (m, 4H, Ar),
6.71 (t, J=2.0 Hz, 2H, pyrrole),
6.18 (t, J=2.0 Hz, 2H, pyrrole),
4.89 (dd, J=8.0, 7.6 Hz, 1H, 2-H),
3.49 (dd, J=14.0, 8.0 Hz, 1H, 3-CH2),
3.26 (dd, J=14.0, 7.6 Hz, 1H, 3-CH2);

13C NMR (CDCl3): δ169.1 (1), 136.1, 134.0, 133.9, 133.79, 133.76, 131.0, 130.9, 129.2, 129.03, 128.99, 128.9, 128.8, 128.6, 127.0, 126.8, 126.7, 126.1, 125.9, 125.8, 125.5, 125.29, 125.26, 123.2, 123.1, 120.1 (pyrrole), 109.0 (pyrrole), 72.3 (1'), 63.5 (2), 38.6 (3);

HR MS: calcd for C34H27NO2Na (M+Na+) 504.1934, found 504.1911.

Incidentally, the enantiomeric excess of Compound 2s was determined after Compound 2s was reduced with LiAlH4 and converted into the corresponding alcohol 2s'.

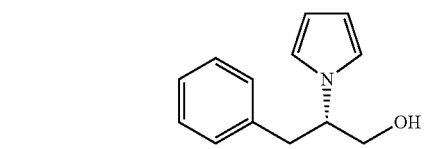 [SMILES: OC[C@H](Cc1ccccc1)n1cccc1]

(S)-3-Phenyl-2-(1H-pyrrol-1-yl)propan-1-ol (2s')

HPLC (CHIRALPAK AD-H, i-PrOH/hexane=1/50, flow rate=0.75 mL/min): tR=26.1 min (93.5%), tR=48.2 min (6.5%);

1H NMR (CDCl3): δ
7.34-7.13 (m, 3H, Ar),
7.08-6.94 (m, 2H, Ar),
6.70 (t, J=2.0 Hz, 2H, pyrrole),
6.17 (t, J=2.0 Hz, 2H, pyrrole), 4.20 (tt, J=7.6, 6.0 Hz, 1H, 2-H),
3.83 (dd, J=6.4, 6.0 Hz, 2H, 1-CH2),
3.06 (d, J=7.6 Hz, 2H, 3-CH2),
1.47 (t, J=6.4 Hz, 1H, OH);
13C NMR (CDCl3): δ137.5, 128.8, 128.5, 126.6, 119.2 (pyrrole), 108.4 (pyrrole), 65.3, 63.5, 38.5 (3);
HR MS: calcd for C13H15NONa (M+Na+) 224.1046, found 224.1044.

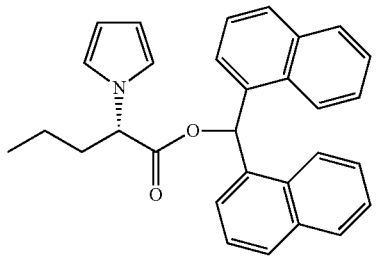 [SMILES: CCC[C@@H](C(=O)OC(c1cccc2ccccc12)c1cccc2ccccc12)n1cccc1]

Di(1-naphthyl)methyl (S)-2-(1H-pyrrol-1-yl)pentanoate (2t) [in Table 6, Entry 3; 89% Yield, 74% ee]

1H NMR (CDCl3): δ
8.39 (s, 1H, 1'-H),
8.03-7.74 (m, 6H, Ar),
7.57-7.24 (m, 6H, Ar),
7.14 (d, J=7.2 Hz, 1H, Ar),
7.04 (d, J=7.2 Hz, 1H, Ar),
6.71 (t, J=2.0 Hz, 2H, pyrrole),
6.19 (t, J=2.0 Hz, 2H, pyrrole),
4.66 (dd, J=9.2, 6.4 Hz, 1H, 2-H),
2.21-1.93 (m, 2H, 3-CH2),
1.32-1.18 (m, 2H, 4-CH2),
0.85 (t, J=7.2 Hz, 3H, 5-CH3);
13C NMR (CDCl3): δ169.9 (1), 134.3, 134.1, 133.83, 133.78, 131.0, 130.9, 129.2, 129.0, 128.9, 128.8, 126.7, 126.6, 126.1, 125.9, 125.8, 125.6, 125.3, 125.3, 123.2, 123.2, 120.0 (pyrrole), 108.7 (pyrrole), 71.9 (1'), 61.8 (2), 34.0 (3), 19.0 (4), 13.4 (5);
HR MS: calcd for C30H27NO2Na (M+Na+) 456.1934, found 456.1932.

Incidentally, the enantiomeric excess of Compound 2t was determined after Compound 2t was reduced with LiAlH4, acylated with p-nitrobenzoyl chloride, and converted into the corresponding p-nitrobenzoic acid ester 2t'.

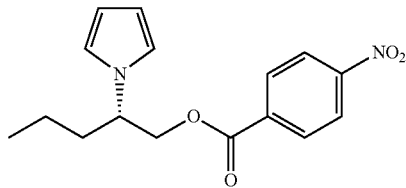

(S)-2-(1H-Pyrrol-1-yl)pentyl 4-nitrobenzoate (2t')

HPLC (CHIRALCEL OD-H, i-PrOH/hexane=1/50, flow rate=1.0 mL/min): tR=15.7 min (13.2%), tR=18.8 min (86.8%);
1H NMR (CDCl3): δ
8.27 (d, J=8.8 Hz, 2H, Ar),
8.09 (d, J=8.8 Hz, 2H, Ar),
6.73 (t, J=2.0 Hz, 2H, pyrrole),
6.18 (t, J=2.0 Hz, 2H, pyrrole),
4.57 (dd, J=11.2, 4.4 Hz, 1H, 1-CH2),
4.48 (dd, J=11.2, 8.0 Hz, 1H, 1-CH2),
4.35-4.22 (m, 1H, 2-H),
1.96-1.75 (m, 2H, 3-CH2),
1.39-1.25 (m, 2H, 4-CH2),
0.94 (t, J=7.2 Hz, 3H, 5-CH3);
13C NMR (CDCl3): δ164.4, 150.4, 130.7, 123.6, 119.1 (pyrrole), 108.4 (pyrrole), 68.3 (1), 58.3 (2), 34.0 (3), 19.1 (4), 13.7 (5);
HR MS: calcd for C16H18N2O4Na (M+Na+) 325.1159, found 325.1164.

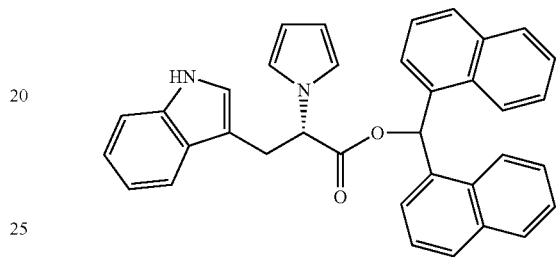

Di(1-naphthyl)methyl (S)-3-(1H-indol-3-yl)-2-(1H-pyrrol-1-yl)propanoate (2u) [in Table 6, Entry 18; 59% Yield, 84% ee]

1H NMR (CDCl3): δ
8.35 (s, 1H, 1'-H),
7.96-7.64 (m, 7H, Ar),
7.57-7.12 (m, 9H, Ar),
7.11-7.03 (m, 1H, Ar),
6.99-6.88 (m, 2H, Ar),
6.80-6.70 (m, 2H, pyrrole),
6.49 (d, J=2.0 Hz, 1H, indole-2"),
6.24-6.12 (m, 2H, pyrrole),
4.99 (t, J=7.6 Hz, 1H, 2-H),
3.68 (dd, J=14.8, 7.6 Hz, 1H, 3-CH2),
3.39 (dd, J=14.8, 7.6 Hz, 1H, 3-CH2);
13C NMR (CDCl3): δ169.6 (1), 135.9, 134.0, 133.9, 133.7, 133.7, 130.9, 130.8, 129.1, 129.0, 128.81, 128.77, 126.9, 126.7, 126.7, 126.0, 125.84, 125.79, 125.6, 125.2, 125.2, 123.21, 123.18, 123.0, 122.1, 120.1 (pyrrole), 119.6, 118.2, 111.1, 109.9, 108.8, 72.1 (1'), 62.4 (2), 28.3 (3);
HR MS: calcd for C36H28N2O2Na (M+Na+) 543.2043, found 543.2018.

Incidentally, the enantiomeric excess of Compound 2u was determined after Compound 2u was reduced with LiAlH4 and converted into the corresponding alcohol 2u'.

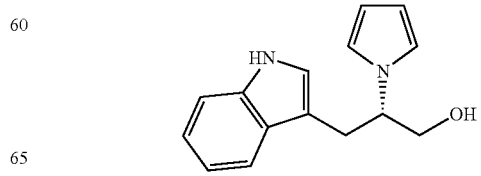

(S)-3-(1H-Indol-3-yl)-2-(1H-pyrrol-1-yl)propan-1-ol (2u')

HPLC (CHIRALPAK AD-H, i-PrOH/hexane=1/9, flow rate=0.75 mL/min): tR=26.1 min (91.8%), tR=36.0 min (8.2%);
1H NMR (DMSO-d6): δ
10.73 (s, 1H, indole-1'),
7.48 (d, J=7.5 Hz, 1H, indole),
7.30 (d, J=7.5 Hz, 1H, indole),
7.04 (dd, J=7.5, 7.5 Hz, 1H, indole),
6.96 (dd, J=7.5, 7.5 Hz, 1H, indole),
6.83-6.71 (m, 3H, indole, pyrrole),
6.01-5.85 (m, 2H, pyrrole),
4.90 (t, J=5.5 Hz, 1H, OH),
4.21 (ddt, J=8.5, 6.5, 5.5 Hz, 1H, 2-H),
3.66 (dd, J=5.5, 5.5 Hz, 2H, 1-CH2),
3.25 (dd, J=14.5, 6.5 Hz, 1H, 3-H),
3.03 (dd, J=14.5, 8.5 Hz, 1H, 3-H);
13C NMR (DMSO-d6): δ135.9, 127.3, 123.1, 120.8, 119.4, 118.2, 118.1, 111.3, 110.7, 106.9, 64.3 (1), 62.0 (2), 27.8 (3);
HR MS: calcd for C15H16N2ONa (M+Na+) 263.1155, found 263.1156.

Di(1-naphthyl)methyl (S)-3-(1-(tert-butoxycarnonyl)-1H-indol-3-yl)-2-(1H-pyrrol-1-yl)propanoate (2v) [in Table 6, Entry 19; 93% Yield, 89% ee]

HPLC (CHIRALPAK IA-3, i-PrOH/hexane=1/9, flow rate=0.5 mL/min): tR=12.2 min (5.6%), tR=14.5 min (94.4%);
1H NMR (CDCl3): δ
8.35 (s, 1H, 1'-H),
7.90-7.68 (m, 6H, Ar),
7.86 (d, J=7.2 Hz, 1H, indole-7'),
7.50-7.14 (m, 9H, Ar),
7.01 (s, 1H, indole-2'),
6.95 (d, J=6.8 Hz, 1H, Ar),
6.91 (d, J=7.2 Hz, 1H, Ar),
6.77 (t, J=2.0 Hz, 2H, pyrrole),
6.21 (t, J=2.0 Hz, 2H, pyrrole),
5.02 (t, J=7.6 Hz, 1H, 2-H),
3.63 (dd, J=14.8, 7.6 Hz, 1H, 3-CH2),
3.33 (dd, J=14.8, 7.6 Hz, 1H, 3-CH2),
1.61 (s, 9H, t-Bu);
13C NMR (CDCl3): δ169.2 (1), 149.4 (Boc), 135.3, 133.9, 133.8, 133.69, 133.67, 130.9, 130.8, 129.8, 129.2, 129.0, 128.84, 128.75, 126.7, 126.6, 125.94, 125.85, 125.8, 125.5, 125.2, 125.1, 124.5, 124.2, 123.1, 123.0, 122.6, 120.0 (pyrrole), 118.5, 115.3, 114.7, 109.1 (pyrrole), 83.5 (t-Bu), 72.3 (1'), 61.7 (2), 28.12 (t-Bu), 28.07 (3);
HR MS: calcd for C41H36N2O4Na (M+Na+) 643.2567, found 643.2551.

Di(1-naphthyl)methyl (S)-3-(4-(methanesulfonyloxy)phenyl)-2-(1H-pyrrol-1-yl)propanoate (2w) [in Table 6, Entry 13; 61% Yield, 88% ee]

HPLC (CHIRALPAK IA-3, i-PrOH/hexane=2/8, flow rate=0.75 mL/min): tR=30.3 min (5.8%), tR=32.9 min (94.2%);
1H NMR (CDCl3): δ
8.35 (s, 1H, 1'-H),
7.93-7.74 (m, 5H, Ar),
7.70 (d, J=8.4 Hz, 1H, Ar),
7.54-7.18 (m, 6H, Ar),
7.12-6.98 (m, 5H, Ar),
6.95 (d, J=7.2 Hz, 1H, Ar),
6.69 (t, J=2.0 Hz, 2H, pyrrole),
6.18 (t, J=2.0 Hz, 2H, pyrrole),
4.84 (dd, J=8.0, 7.6 Hz, 1H, 2-H),
3.48 (dd, J=14.0, 7.6 Hz, 1H, 3-CH2),
3.24 (dd, J=14.0, 8.0 Hz, 1H, 3-CH2),
3.04 (s, 3H, Ms);
13C NMR (CDCl3): δ168.8 (1), 148.1, 135.5, 133.8, 133.73, 133.67, 130.9, 130.7, 130.6, 130.6, 129.3, 129.0, 128.9, 128.8, 126.8, 126.7, 126.1, 125.9, 125.8, 125.3, 125.2, 123.1, 122.9, 122.0, 122.0, 120.0 (pyrrole), 109.2 (pyrrole), 72.3 (1'), 63.1 (2), 37.8 (Ms), 37.2 (Ms);
HR MS: calcd for C35H29NO5SNa (M+Na+) 598.1659, found 598.1663.

Di(1-naphthyl)methyl (S)-3-(3,4-bis(methanesulfonyloxy)phenyl)-2-(1H-pyrrol-1-yl)propanoate (2x) [in Table 6, Entry 14; 97% Yield, 83% ee]

HPLC (CHIRALPAK ID, i-PrOH/hexane=2/8, flow rate=0.75 mL/min): tR=29.9 min (8.5%), tR=32.6 min (91.5%);
1H NMR (CDCl3): δ
8.39 (s, 1H, 1'-H),
8.02-7.66 (m, 6H, Ar),
7.55-7.39 (m, 3H, Ar),
7.37-7.20 (m, 4H, Ar), 7.09 (d, J=6.8 Hz, 1H, Ar),
7.03-6.85 (m, 3H, Ar),
6.65 (t, J=2.0 Hz, 2H, pyrrole),
6.16 (t, J=2.0 Hz, 2H, pyrrole),
4.83 (dd, J=9.2, 6.4 Hz, 1H, 2-H),
3.44 (dd, J=14.0, 6.4 Hz, 1H, 3-CH2),
3.27 (dd, J=14.0, 9.2 Hz, 1H, 3-CH2),
3.15 (s, 3H, Ms), 3.05 (s, 3H, Ms);

13C NMR (CDCl3): δ168.5 (1), 140.8, 139.9, 137.1, 133.78, 133.76, 133.7, 133.6, 130.9, 130.6, 129.4, 129.1, 129.0, 128.81, 128.77, 128.77, 127.0, 126.7, 126.3, 126.0, 125.8, 125.2, 125.2, 124.3, 124.2, 123.0, 122.8, 120.1 (pyrrole), 109.4 (pyrrole), 72.4 (1'), 62.7 (2), 38.4 (Ms), 38.3 (Ms), 37.8 (3);

HR MS: calcd for C36H31NO8S2Na (M+Na+) 692.1383, found 692.1412.

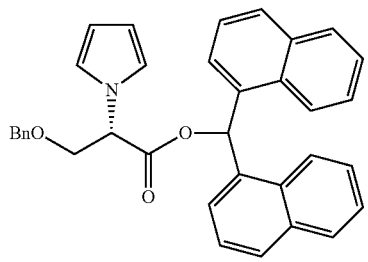 [SMILES: O=C(OC(c1cccc2ccccc12)c1cccc2ccccc12)[C@H](COCc1ccccc1)n1cccc1]

Di(1-naphthyl)methyl (S)-3-benzyloxy-2-(1H-pyrrol-1-yl)propanoate (2y) [in Table 6, Entry 8; 79% Yield, 64% ee]

1H NMR (CDCl3): δ
8.41 (s, 1H, 1'-H),
7.97-7.80 (m, 6H, Ar),
7.50-7.11 (m, 13H, Ar),
6.75 (t, J=2.1 Hz, 2H, pyrrole),
6.18 (t, J=2.1 Hz, 2H, pyrrole),
4.94 (t, J=6.0 Hz, 1H, 2-H),
4.42 (d, J=12.0 Hz, 2H, Bn),
4.06 (dd, J=9.8, 6.0 Hz, 1H, 3-CH2),
3.96 (dd, J=9.8, 6.0 Hz, 1H, 3-CH2). Incidentally, the enantiomeric excess of Compound 2y was determined after Compound 2y was reduced with LiAlH4, acylated with p-nitrobenzoyl chloride, and converted into the corresponding p-nitrobenzoic acid ester 2y'.

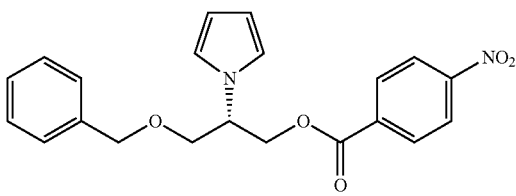 [SMILES: O=C(OC[C@H](COCc1ccccc1)n1cccc1)c1ccc([N+](=O)[O-])cc1]

(S)-3-(benzyloxy)-2-(1H-pyrrol-1-yl)propyl 4-nitrobenzoate (2y')

HPLC (CHIRALPAK AD-H, i-PrOH/hexane=1/9, flow rate=0.7 mL/min): tR=22.7 min (82.1%), tR=24.3 min (17.9%);

1H NMR (CDCl3): δ
8.25 (d, J=8.8 Hz, 2H, Ar),
8.06 (d, J=8.8 Hz, 2H, Ar),
8.04-7.26 (m, 5H, Ar),
6.78 (t, J=2.0 Hz, 2H, pyrrole),
6.18 (t, J=2.0 Hz, 2H, pyrrole),
4.74 (dd, J=11.2, 4.8 Hz, 1H, 1-CH2),
4.69 (dd, J=11.2, 7.6 Hz, 1H, 1-CH2),
4.54 (d, J=12.0 Hz, 2H, Bn)
4.57-4.50 (m, 1H, 2-H),
3.88 (dd, J=9.8, 6.0 Hz, 1H, 3-CH2),
3.85 (dd, J=9.8, 5.2 Hz, 1H, 3-CH2), 13C NMR (CDCl3): δ164.2 (1'), 150.6, 137.4, 135.0, 130.7, 128.5, 127.9, 127.7, 123.6, 119.8 (pyrrole), 108.7 (pyrrole), 73.5 (Bn), 69.8 (3), 65.6 (2), 57.9 (1);

IR (KBr): 3109, 3062, 3031, 2916, 2862, 1959, 1728, 1527, 1350, 1273, 1103, 725 cm-1.

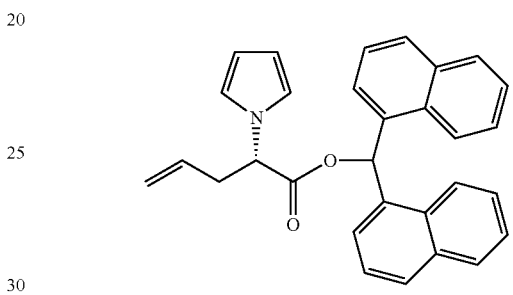

Di(1-naphthyl)methyl (S)-2-(1H-pyrrol-1-yl)-4-pentenoate (2z) [In Table 6, entry 9; 93% yield, 85% ee]

HPLC (CHIRALPAK AD-H, i-PrOH/hexane=1/99, flow rate=0.5 mL/min): tR=28.8 min (7.4%), tR=30.2 min (92.6%);

1H NMR (CDCl3): δ
8.43 (s, 1H, 1'-H),
8.02-7.23 (m, 6H, Ar),
7.55-7.07 (m, 8H, Ar),
6.76 (t, J=2.2 Hz, 2H, pyrrole),
6.24 (t, J=2.2 Hz, 2H, pyrrole),
5.66 (ddt, J=17.0, 10.0, 6.8 Hz, 1H, 4-H),
5.09 (ddd, J=17.0, 2.6, 1.6 Hz, 1H, 5-CH2),
5.05 (ddd, J=10.0, 2.6, 1.2 Hz, 1H, 5-CH2),
2.98-2.76 (m, 2H, 3-CH2);

13C NMR (CDCl3): δ169.2 (1), 134.1, 133.9, 133.8, 133.7, 132.1, 131.0, 130.8, 129.3, 129.0, 128.9, 128.8, 126.8, 126.6, 126.2, 125.9, 125.8, 125.5, 125.26, 125.25, 123.22, 123.17, 120.0 (pyrrole), 118.9, 108.9 (pyrrole), 72.1 (1'), 61.7 (2), 36.2 (3);

HR MS: calcd for C30H25NO2Na (M+Na+) 454.1778, found 454.1789. IR (KBr): 3062, 3016, 2931, 1743, 1550, 1389, 1164, 941, 756 cm-1.

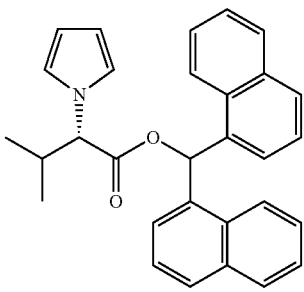 [SMILES: CC(C)[C@@H](C(=O)OC(c1cccc2ccccc12)c1cccc2ccccc12)n1cccc1]

Di(1-naphthyl)methyl (S)-3-methyl-2-(1H-pyrrole-1-yl)butanoate (2aa) [in Table 6, Entry 4; 38% Yield, 91% ee]

HPLC (CHIRALPAK OD-H×2, i-PrOH/hexane=1/9, flow rate=0.5 mL/min): tR=19.5 min (95.5%), tR=23.5 min (4.5%);
1H NMR (CDCl3): δ
8.38 (s, 1H, 1'-H),
8.03-7.70 (m, 6H, Ar),
7.53-7.20 (m, 6H, Ar),
7.11 (d, J=7.2 Hz, 1H, Ar),
7.01 (d, J=7.2 Hz, 1H, Ar),
6.71 (t, J=2.0 Hz, 2H, pyrrole),
6.18 (t, J=2.0 Hz, 2H, pyrrole),
4.22 (d, J=10.4 Hz, 1H, 2-H),
2.95-2.36 (m, 1H, 3-H),
0.97 (d, J=6.4 Hz, 3H, 4-CH3)
0.75 (d, J=6.4 Hz, 3H, 4-CH3);
13C NMR (CDCl3): δ169.4 (1), 134.2, 134.0, 133.81, 133.76, 131.0, 130.9, 129.2, 129.0, 128.9, 128.8, 126.7, 126.6, 126.1, 125.9, 125.8, 125.5, 125.2, 125.2, 123.22, 123.18, 120.3 (pyrrole), 108.6 (pyrrole), 71.9 (1'), 69.1 (2), 30.9 (3), 19.5 (4), 18.5 (4);
HR MS: calcd for C30H27NO2Na (M+Na+) 456.1934, found 456.1932;
IR (KBr): 3061, 2967, 2873, 1740, 1599, 1509, 1486, 1180, 783, 735 cm-1.
Mp: 149-152° C. (CHCl3/hexane)

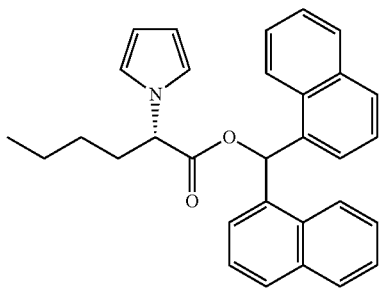 [SMILES: CCCC[C@@H](C(=O)OC(c1cccc2ccccc12)c1cccc2ccccc12)n1cccc1]

Di(1-naphthyl)methyl (S)-2-(1H-pyrrole-1-yl)hexanoate (2bb) [in Table 6, Entry 5; Quantitative Yield, 79% ee]

HPLC (CHIRALPAK AD-H, i-PrOH/hexane=2/98, flow rate=0.5 mL/min): tR=20.1 min (10.3%), tR=21.7 min (89.7%);
1H NMR (CDCl3): δ
8.38 (s, 1H, 1'-H),
7.97-7.79 (m, 6H, Ar),
7.50-7.03 (m, 8H, Ar),
6.71 (t, J=2.1 Hz, 2H, pyrrole),
6.19 (t, J=2.1 Hz, 2H, pyrrole),
4.64 (dd, J=9.2, 6.6 Hz, 1H, 2-H),
2.14 (ddt, J=20.4, 9.2, 3.2 Hz, 1H, 3-CH2),
2.00 (ddt, J=20.4, 6.6, 3.2 Hz, 1H, 3-CH2),
1.31-1.15 (m, 4H, 3-CH2, 4-CH2),
0.80 (t, J=7.0 Hz, 3H, 6-CH3);
13C NMR (CDCl3): δ169.9 (1), 134.3, 134.1, 133.82, 133.76, 131.0, 130.9, 129.2, 129.1, 128.9, 128.8, 126.7, 126.6, 126.1, 125.9, 125.8, 125.6, 125.3, 123.2, 120.0 (pyrrole), 108.7 (pyrrole), 71.9 (1'), 62.1 (2), 31.8 (3), 27.9 (4), 22.1 (5), 13.7 (6);
HR MS: calcd for C31H29NO2Na (M+Na+) 470.2091, found 470.2103;
IR (KBr): 3052, 2958, 2929, 2862, 1745, 1599, 1510, 1488, 1162, 796, 721 cm-1. Mp: 108-109° C. (CH2Cl2/hexane)

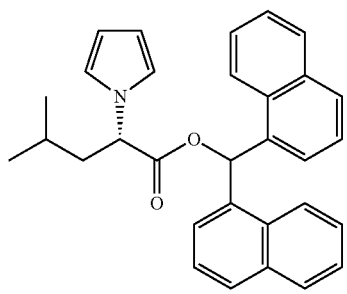 [SMILES: CC(C)C[C@@H](C(=O)OC(c1cccc2ccccc12)c1cccc2ccccc12)n1cccc1]

Di(1-naphthyl)methyl (S)-4-methyl-2-(1H-pyrrole-1-yl)hexanoate (2cc) [in Table 6, Entry 6; 90% Yield, 74% ee]

1H NMR (CDCl3): δ
8.37 (s, 1H, 1'-H),
7.97-7.80 (m, 6H, Ar),
7.51-7.01 (m, 8H, Ar),
6.71 (t, J=2.2 Hz, 2H, pyrrole),
6.19 (t, J=2.2 Hz, 2H, pyrrole),
4.75 (dd, J=8.8, 6.8 Hz, 1H, 2-H),
1.97 (ddd, J=12.0, 8.8, 3.8 Hz, 1H, 3-CH2),
1.95 (ddd, J=12.0, 6.8, 3.8 Hz, 1H, 3-CH2),
1.47 (qqt, J=6.4, 6.4, 3.8 Hz, 1H, 4-H),
0.86 (d, J=6.4 Hz, 6H, 5-CH3);
13C NMR (CDCl3): δ170.0 (1), 134.2, 134.1, 133.81, 133.76, 131.0, 130.9, 129.2, 129.0, 128.9, 128.8, 126.7, 126.6, 126.1, 125.9, 125.8, 125.6, 125.3, 123.1, 120.1 (pyrrole), 108.7 (pyrrole), 71.9 (1'), 60.3 (2), 40.9 (3), 24.6 (4), 22.6 (5), 21.8 (5);
HR MS: calcd for C31H30NO2 (M+H+) 448.2271, found 448.2270;
IR (KBr): 3057, 2957, 2931, 1749, 1597, 1509, 1173, 961, 774, 723 cm-1;
Mp: 133-135° C. (CH2Cl2/hexane)

Incidentally, the enantiomeric excess of Compound 2cc was determined after Compound 2cc was reduced with LiAlH4, acylated with p-nitrobenzoyl chloride, and converted into the corresponding p-nitrobenzoic acid ester 2cc'.

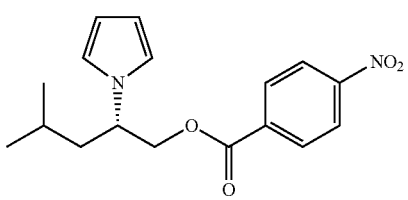 [SMILES: CC(C)C[C@@H](COC(=O)c1ccc([N+](=O)[O-])cc1)n1cccc1]

(S)-4-methyl-2-(1H-pyrrol-1-yl)pentyl 4-nitrobenzoate (2cc')

HPLC (CHIRALPAK OD-H, i-PrOH/hexane=1/9, flow rate=0.5 mL/min): tR=16.5 min (13.2%), tR=18.2 min (86.8%);

1H NMR (CDCl3): δ
8.26 (d, J=8.8 Hz, 2H, Ar),
8.08 (d, J=8.8 Hz, 2H, Ar),
8.01-7.20 (m, 7H, Ar),
6.73 (t, J=2.2 Hz, 2H, pyrrole),
6.17 (t, J=2.2 Hz, 2H, pyrrole),
4.55 (dd, J=11.2, 4.4 Hz, 1H, 1-CH2),
4.45 (dd, J=11.2, 8.4 Hz, 1H, 1-CH2),
4.41-4.34 (m, 1H, 2-H),
1.91 (dd, J=10.2, 4.8 Hz, 1H, 3-CH2),
1.88 (dd, J=10.2, 4.8 Hz, 1H, 3-CH2),
1.64-1.46 (m, 2H, 3-CH2, 4-H),
0.95 (d, J=6.4 Hz, 3H, 5-CH3),
0.92 (d, J=6.4 Hz, 3H, 5-CH3);

13C NMR (CDCl3): δ164.3 (1'), 150.7, 135.2, 130.7, 123.6, 119.1 (pyrrole), 108.4 (pyrrole), 68.6 (1), 56.6 (2), 40.7 (3), 24.5 (4), 23.0 (5), 21.8 (5);

HR MS: calcd for C17H21N2O4 (M+H+) 317.1496, found 317.1502;

IR (KBr): 3108, 3074, 2955, 2933, 2869, 1729, 1520, 1270, 1119, 719 cm-1.

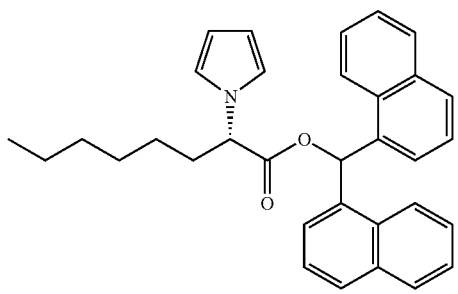 [SMILES: CCCCCC[C@@H](C(=O)OC(c1cccc2ccccc12)c1cccc2ccccc12)n1cccc1]

Di(1-naphthyl)methyl (S)-2-(1H-pyrrol-1-yl)octanoate (2dd) [in Table 6, Entry 7; Quantitative Yield, 79% ee]

HPLC (CHIRALPAK AD-H, i-PrOH/hexane=1/9, flow rate=0.7 mL/min): tR=7.8 min (10.5%), tR=8.2 min (89.5%);

1H NMR (CDCl3): δ
8.38 (s, 1H, 1'-H),
7.97-7.80 (m, 6H, Ar),
7.52-7.04 (m, 8H, Ar),
6.71 (t, J=2.0 Hz, 2H, pyrrole),
6.19 (t, J=2.0 Hz, 2H, pyrrole),
4.64 (dd, J=8.8, 6.8 Hz, 1H, 2-H),
2.13 (ddt, J=14.0, 8.8, 5.2 Hz, 1H, 3-CH2),
2.00 (ddt, J=14.0, 6.8, 5.2 Hz, 1H, 3-CH2),
1.23-1.15 (m, 8H, 4-CH2, 5-CH2, 6-CH2, 7-CH2),
0.83 (t, J=7.0 Hz, 3H, 8-CH3);

13C NMR (CDCl3): δ169.9 (1), 134.3, 134.1, 133.81, 133.76, 131.0, 130.9, 129.2, 129.1, 128.9, 128.8, 126.7, 126.6, 126.1, 125.9, 125.8, 125.6, 125.3, 123.2, 120.0 (pyrrole), 108.7 (pyrrole), 71.9 (1'), 62.1 (2), 32.1 (3), 31.5 (4), 28.7 (5), 25.7 (6), 22.4 (7), 13.98 (8);

HR MS: calcd for C33H33NO2Na (M+Na+) 498.2404, found 498.2421;

IR (KBr): 3052, 2954, 2926, 2856, 1737, 1598, 1509, 1159, 1092, 796, 719 cm-1;

Mp: 96-97° C. (CH2Cl2/hexane)

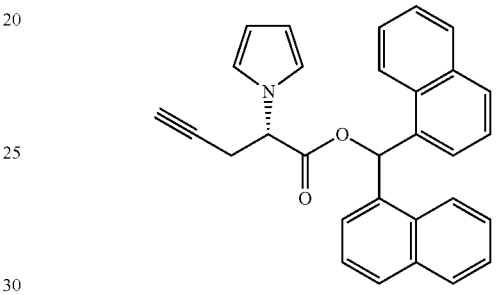

Di(1-naphthyl)methyl 2-(1H-pyrrol-1-yl)pent-4-ynoate (2ee) [in Table 6, Entry 10; Quantitative Yield, ee 94%]

HPLC (CHIRALPAK AD-H, i-PrOH/hexane=2/98, flow rate=0.5 mL/min): tR=31.5 min (2.9%), tR=43.3 min (97.1%);

1H NMR (CDCl3): δ
8.40 (s, 1H, 1'-H),
8.03-7.73 (m, 6H, Ar),
7.52-7.01 (m, 8H, Ar),
6.72 (t, J=2.1 Hz, 2H, pyrrole),
6.20 (t, J=2.1 Hz, 2H, pyrrole),
4.87 (t, J=7.6 Hz, 1H, 2-H),
3.04 (ddd, J=16.8, 7.6, 2.6 Hz, 1H, 3-CH2),
2.90 (ddd, J=16.8, 7.6, 2.6 Hz, 1H, 3-CH2),
1.96 ((t, J=2.6 Hz, 1H, 5-H);

13C NMR (CDCl3): δ168.1 (1), 133.91, 133.86, 133.7, 131.8, 131.4, 130.9, 130.8, 129.1, 129.0, 128.9, 128.8, 127.9, 127.5, 126.74, 126.69, 126.4, 125.99, 125.9, 125.8, 125.64, 125.56, 125.4, 125.3, 125.2, 123.2, 123.1, 122.8, 120.1 (pyrrole), 109.0 (pyrrole), 72.3 (1'), 62.4 (2), 35.8 (3);

HR MS: calcd for C30H24NO2Na (M+Na+) 430.1802, found 430.1817;

IR (KBr): 3054, 3010, 2958, 1738, 1598, 1510, 1273, 1157, 944, 777, 731 cm-1.

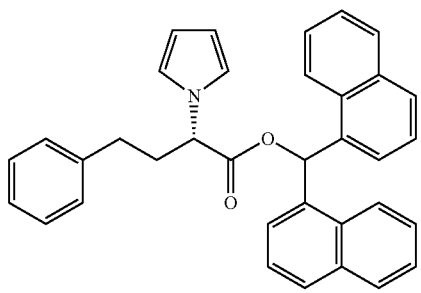 [SMILES: O=C(OC(c1cccc2ccccc12)c1cccc2ccccc12)[C@H](CCc1ccccc1)n1cccc1]

Di(1-naphthyl)methyl (S)-4-phenyl-2-(1H-pyrrol-1-yl)butanoate (2ff) [in Table 6, Entry 12; 81% Yield, 65% ee]

1H NMR (CDCl3): δ
8.40 (s, 1H, 1'-H),
8.00-7.87 (m, 6H, Ar),
7.85-7.00 (m, 13H, Ar),
6.71 (t, J=2.1 Hz, 2H, pyrrole),
6.22 (t, J=2.1 Hz, 2H, pyrrole),
4.61 (dd, J=9.2, 6.0 Hz, 1H, 2-H),
2.60-2.29 (m, 4H, 3-CH2, 4-CH2);
13C NMR (CDCl3): δ169.6 (1), 140.0, 134.2, 134.0, 133.84, 133.76, 131.0, 130.8, 129.3, 129.04, 128.96, 128.8, 128.5, 126.8, 126.7, 126.3, 126.2, 125.9, 125.8, 125.5, 125.3, 123.18, 123.16, 120.1 (pyrrole), 108.9 (pyrrole), 71.98 (1'), 60.98 (2), 33.4 (3), 31.6 (4);
HR MS: calcd for C35H29NO2Na (M+Na+) 518.2091, found 518.2077;
IR (KBr): 3052, 3025, 2956, 2925, 2858, 1737, 1626, 1490, 1285, 1174, 794, 728 cm-1;
Mp: 114-115° C. (CH2Cl2/hexane)

Incidentally, the enantiomeric excess of Compound 2ff was determined after Compound 2ff was reduced with LiAlH4, acylated with p-nitrobenzoyl chloride, and converted into the corresponding p-nitrobenzoic acid ester 2ff'.

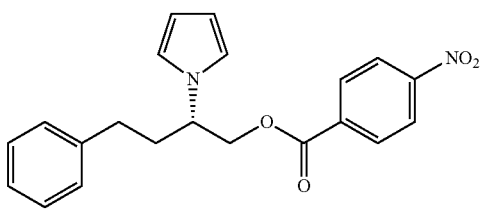 [SMILES: O=C(OC[C@H](CCc1ccccc1)n1cccc1)c1ccc([N+](=O)[O-])cc1]

(S)-4-phenyl-2-(1H-pyrrol-1-yl)butyl 4-nitrobenzoate (2ff')

HPLC (CHIRALPAK AD-H, i-PrOH/hexane=1/9, flow rate=0.5 mL/min): tR=21.9 min (82.5%), tR=27.9 min (17.5%);
1H NMR (CDCl3): δ
8.26 (d, J=8.8 Hz, 2H, Ar),
8.07 (d, J=8.8 Hz, 2H, Ar),
7.32-7.13 (m, 5H, Ar),
6.75 (t, J=2.2 Hz, 2H, pyrrole),
6.22 (t, J=2.2 Hz, 2H, pyrrole),
4.54 (dd, J=11.6, 5.2 Hz, 1H, 1-CH2),
4.49 (dd, J=11.6, 7.4 Hz, 1H, 1-CH2),
4.24 (dddd, J=10.4, 7.4, 5.0, 4.8 Hz, 1H, 2-H),
2.68-2.48 (m, 2H, 4-CH2)
2.28-2.16 (m, 2H, 3-CH2);
13C NMR (CDCl3): δ164.2 (1'), 150.6, 140.4, 135.0, 130.7, 128.6, 128.5, 126.3, 123.6, 119.1 (pyrrole), 108.7 (pyrrole), 68.2 (1), 57.5 (2), 33.4 (3), 31.7 (4);
IR (KBr): 3109, 3062, 3024, 2931, 2862, 1952, 1728, 1527, 1273, 1103, 717 cm-1

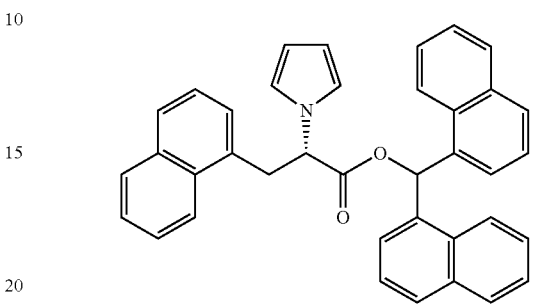

Di (1-naphthyl) methyl (S)-3-(naphth-1-yl)-2-(1H-pyrrol-1-yl) propanoate (2gg) [In Table 6, Entry 15; Yield 76%, 86% ee]

1H NMR (CDCl3): δ
8.34 (s, 1H, 1'-H),
7.92-7.70 (m, 9H, Ar),
7.47-6.92 (m, 12H, Ar),
6.74 (t, J=2.0 Hz, 2H, pyrrole),
6.19 (t, J=2.0 Hz, 2H, pyrrole),
5.09 (dd, J=7.8, 6.8 Hz, 1H, 2-H),
4.02 (dd, J=14.4, 7.8 Hz, 1H, 3-CH2),
3.66 (dd, J=14.4, 6.8 Hz, 1H, 3-CH2);
13C NMR (CDCl3): δ169.2 (1), 133.91, 133.86, 133.7, 131.8, 131.4, 130.9, 130.8, 129.1, 129.0, 128.9, 128.8, 127.9, 127.5, 126.74, 126.69, 126.4, 125.99, 125.9, 125.8, 125.64, 125.56, 125.4, 125.3, 125.2, 123.2, 123.1, 122.8, 120.1 (pyrrole), 109.0 (pyrrole), 72.3 (1'), 62.4 (2), 35.8 (3);
IR (KBr): 3054, 3010, 2958, 1738, 1598, 1510, 1273, 1157, 944, 777, 731 cm-1.

Incidentally, the enantiomeric excess of Compound 2gg was determined after Compound 2gg was reduced with LiAlH4, acylated with p-nitrobenzoyl chloride, and converted into the corresponding p-nitrobenzoic acid ester 2gg'.

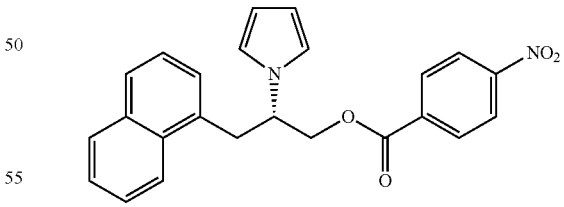

(S)-3-(naphth-1-yl)-2-(1H-pyrrol-1-yl)propyl 4-nitrobenzoate (2gg')

HPLC (CHIRALPAK AD-H, i-PrOH/hexane=1/9, flow rate=0.5 mL/min): tR=33.6 min (92.9%), tR=36.8 min (7.1%);
1H NMR (CDCl3): δ
8.24 (d, J=8.8 Hz, 2H, Ar),
8.03 (d, J=8.8 Hz, 2H, Ar), 8.01-7.20 (m, 7H, Ar),
6.77 (t, J=2.0 Hz, 2H, pyrrole),
6.18 (t, J=2.0 Hz, 2H, pyrrole),
4.77-4.70 (m, 1H, 2-H),
4.64 (dd, J=11.2, 6.4 Hz, 1H, 1-CH2),
4.60 (dd, J=11.2, 5.2 Hz, 1H, 1-CH2),
3.70 (dd, J=14.0, 7.6 Hz, 1H, 3-CH2),
3.66 (dd, J=14.0, 6.8 Hz, 1H, 3-CH2);
13C NMR (CDCl3): δ164.1 (1'), 150.6, 134.9, 134.0, 132.7, 131.5, 130.7, 129.2, 127.99, 127.5, 126.5, 125.8, 125.5, 123.6, 122.9, 119.2 (pyrrole), 108.7 (pyrrole), 67.4 (1), 58.8 (2), 36.6 (3);
IR (KBr): 3109, 3055, 3008, 2954, 1952, 1728, 1527, 1273, 1095, 725 cm-1

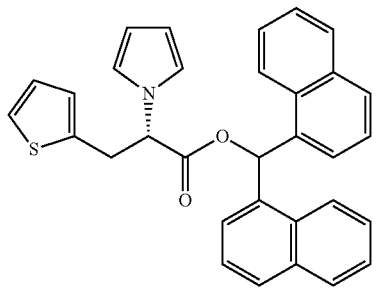 [SMILES: O=C(OC(c1cccc2ccccc12)c1cccc2ccccc12)[C@H](Cc1cccs1)n1cccc1]

Di(1-naphthyl)methyl (S)-2-(1H-pyrrol-1-yl)-3-(thiophen-2-yl)propanoate (2hh) [in Table 6, Entry 16; 97% Yield, 96% ee]

HPLC (CHIRALPAK AD-H, i-PrOH/hexane=1/9, flow rate=0.5 mL/min): tR=15.1 min (2.2%), tR=22.3 min (97.8%);
1H NMR (CDCl3): δ
8.36 (s, 1H, 1'-H),
7.94-7.27 (m, 12H, Ar),
7.12 (dd, J=5.4, 1.2 Hz, 1H, thiophen),
7.03 (d, J=7.2 Hz, 1H, Ar),
6.93 (d, J=7.2 Hz, 1H, Ar),
6.84 (dd, J=5.4, 3.2 Hz, 1H, thiophen),
6.72 (t, J=2.0 Hz, 2H, pyrrole),
6.64 (d, J=3.2 Hz, 1H, thiophen),
6.21 (t, J=2.0 Hz, 2H, pyrrole),
4.89 (t, J=7.6 Hz, 1H, 2-H),
3.74 (dd, J=14.8, 7.6 Hz, 1H, 3-CH2),
3.46 (dd, J=14.8, 7.6 Hz, 1H, 3-CH2);
13C NMR (CDCl3): δ168.8 (1), 137.7, 133.9, 133.80, 133.79, 133.72, 131.0, 130.8, 129.3, 129.0, 128.9, 128.8, 126.92, 126.86, 126.6, 126.5, 126.3, 125.9, 125.8, 125.3, 124.6, 123.2, 123.1, 120.1 (pyrrole), 109.2 (pyrrole), 72.4 (1'), 63.3 (2), 32.7 (3);
HR MS: calcd for C32H25NO2SNa (M+Na+) 510.1498, found 510.1505;
IR (KBr): 3056.1741, 1598, 1509, 1263, 1167, 955, 778, 727 cm-1;
Mp: 120-121° C. (CH2Cl2/hexane).

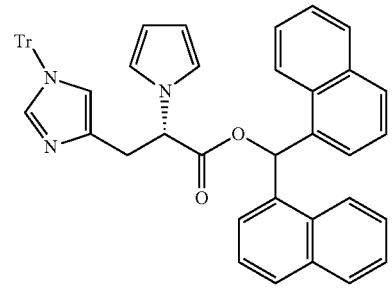

Di(1-naphthyl)methyl (S)-2-(1H-pyrrol-1-yl)-3-(1-trityl-1H-imidazol-4-yl)propanoate (2ii) [in Table 6, Entry 17; 68% Yield, 65% ee]

HPLC (CHIRALPAK AD-H, i-PrOH/hexane=3/7, flow rate=0.75 mL/min): tR=22.6 min (17.3%), tR=23.7 min (82.7%);
1H NMR (CDCl3): δ
8.41 (s, 1H, 1'-H),
7.99 (d, J=8.4 Hz, 1H, Ar),
7.88-7.74 (m, 5H, Ar),
7.49-7.17 (m, 17H, Ar),
7.05 (d, J=7.2 Hz, 1H, Ar),
7.00-6.92 (m, 6H, Ar),
6.63 (t, J=2.0 Hz, 2H, pyrrole),
6.22 (s, 1H, imidazole),
6.11 (t, J=2.0 Hz, 2H, pyrrole),
5.13 (dd, J=10.0, 5.6 Hz, 1H, 2-H),
3.41 (dd, J=14.8, 5.6 Hz, 1H, 3-CH2),
3.19 (d, J=14.8, 10.0 Hz, 1H, 3-CH2);
13C NMR (CDCl3): δ169.3 (1), 149.4, 142.2, 138.1, 135.5, 134.1, 134.0, 133.7, 133.6, 130.9, 130.8, 129.6, 129.1, 128.9, 128.7, 127.8, 126.7, 126.5, 126.1, 125.8, 125.6, 125.5, 125.2, 125.1, 123.1, 123.0, 120.0 (pyrrole), 119.9, 108.4 (pyrrole), 106.4, 75.0 (Tr), 71.8 (1'), 61.7 (2), 31.8 (3);
HR MS: calcd for C50H39N3O2 (M+H+) 714.3115, found 714.3104;
IR (KBr): 3053, 2923, 1741, 1598, 1510, 1486, 1158, 797, 782, 773, 750, 718 cm-1;
Mp: 191-194° C. (AcOEt/hexane)

Test Example 7: Conversion of Optically Active Carboxylic Acid di(1-naphthyl)methyl Ester to Corresponding N-Boc-α-Amino Acid Methyl Ester and di(1-naphthyl)methanol

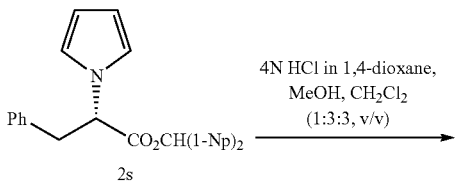

(eq. 1)

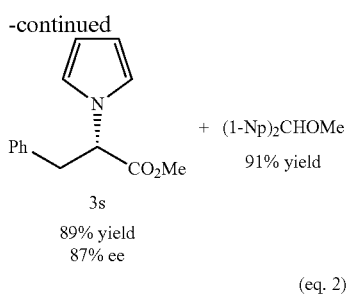

3s
89% yield
87% ee (eq. 2)

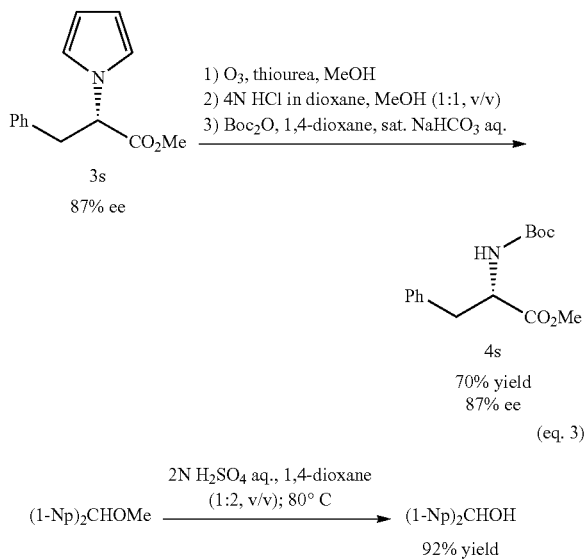

4s
70% yield
87% ee (eq. 3)

$$(1\text{-Np})_2\text{CHOMe} \xrightarrow[\text{(1:2, v/v); 80° C}]{2\text{N H}_2\text{SO}_4 \text{ aq., 1,4-dioxane}} (1\text{-Np})_2\text{CHOH}$$

92% yield

As illustrated in the reaction formula above, it was possible to convert an optically active carboxylic acid di(1-naphthyl)methyl ester 2s (87% ee) obtained by the method which conforms to Test Example 6 (reaction conditions: (1-Np)2CHOH (1.1 eq), Piv2O (3.6 eq), i-Pr2NEt (4.8 eq), and (R)-BTM (5 mol %), DMF (0.2 M) were reacted at room temperature for 24 hours) into an N-Boc-α-amino acid methyl ester 4s and di(1-naphthyl)methanol.

The carboxylic acid di(1-naphthyl)methyl ester 2s is poorly soluble, and thus it was first subjected to transesterification to obtain a soluble carboxylic acid methyl ester 3s at 89% yield. The di(1-naphthyl)methyl ester residue was isolated as di(1-naphthyl)methyl methyl ether at 91% yield (Equation 1). Subsequently, the carboxylic acid methyl ester 3s was subjected to ozonolysis and then protected with Boc, and the N-Boc-phenylalanine methyl ester 4s was obtained at 70% yield while maintaining a high enantiomeric excess (Equation 2, 87% ee). Furthermore, di(1-naphthyl)methyl methyl ether was hydrolyzed to recover di(1-naphthyl)methanol at 92% yield (Equation 3).

Incidentally, with regard to the recovery of di(1-naphthyl) methanol, carboxylic acid di(1-naphthyl)methyl ester was reduced with LiAlH4 to obtain the corresponding alcohol in the report by Birman (X. Yang, V. B. Birman, Angew. Chem. Int. Ed., 2011, 50, 5553-5555), but there is an advantage in the above method that the carbonyl group of the base material is held.

The details of each reaction are as follows.

Transesterification of Carboxylic Acid di(1-naphthyl)methyl Ester 2s 1,4-dioxane (4.0 M, 4.39 mL, 17.6 mmol) was added at 0° C. to a solution prepared by dissolving the carboxylic acid di(1-naphthyl)methyl ester 2s (211 mg, 0.439 mmol) in methanol (13.2 mL) and dichloromethane (13.2 mL). The reaction mixture was stirred for 24 hours at room temperature and then extracted with chloroform, and the organic layer was separated. The organic layer was dried over sodium sulfate, then filtered, and concentrated under reduced pressure, thereby obtaining a crude product. The crude product was separated (developing solvent: toluene) by silica gel thin layer chromatography, thereby obtaining the pale yellow oily carboxylic acid methyl ester 3s (89.6 mg, 89% yield, 87% ee) and a colorless solid di(1-naphthyl) methyl methyl ether (120 mg, 91% yield).

Methyl (S)-3-phenyl-2-(1H-pyrrol-1-yl)propanoate (3s) [87% ee]

HPLC (CHIRALPAK AD-H, i-PrOH/hexane=1/49, flow rate=0.75 mL/min): tR=25.4 min (93.6%), tR=37.6 min (6.4%);
[α]D26-50.6 (c 1.09, CHCl3);
IR (neat): 3030, 2952, 2852, 1745, 1488, 1169, 726 cm-1;
1H NMR (CDCl3): δ
7.29-7.19 (m, 3H, Ar),
7.07-6.98 (m, 2H, Ar),
6.71 (t, 2H, J=2.8 Hz, pyrrole),
6.14 (t, 2H, J=2.8 Hz, pyrrole),
4.75 (dd, J=11.6, 8.8 Hz, 1H, 2-H),
3.70 (s, 3H, OCH3),
3.42 (dd, J=18.4, 8.8 Hz, 1H, 3-CH2),
3.25 (dd, J=18.4, 11.6 Hz, 1H, 3-CH2);
13C NMR (CDCl3): δ170.6 (1), 136.3, 128.8, 128.5, 127.0, 120.1 (pyrrole), 108.7 (pyrrole), 63.5 (2), 52.5 (OCH3), 39.5 (3);
HR MS: calcd for C14H15NO2Na (M+Na+) 252.0995, found 252.1000.

Di (α-naphthyl)methyl Methyl Ether

Mp: 139-141° C. (AcOEt/hexane);
IR (KBr): 2981, 2880, 1595, 1508, 1155, 1092, 815, 790, 777 cm-1;
1H NMR (CDCl3): δ
8.10-7.98 (m, 2H, Ar),
7.93-7.87 (m, 2H, Ar),
7.85-7.78 (m, 2H, Ar),
7.53-7.35 (m, 8H, Ar),
6.72 (s, 1H, 1-H),
3.62 (s, 3H, OCH3);
13C NMR (CDCl3): δ136.0, 134.0, 131.8, 128.8, 128.6, 126.3, 125.8, 125.6, 125.4, 123.7, 79.4 (1), 57.9 (OCH3);
HR MS: calcd for C22H18ONa (M+Na+) 321.1250, found 321.1249.

Ozonolysis and Protection with Boc of Carboxylic Acid Methyl Ester 3s

A solution prepared by dissolving the carboxylic acid methyl ester 3s (85.6 mg, 0.373 mmol) in methanol (15 mL) was treated with ozone for 2 hours at −78° C. Argon gas was allowed to bubble in the reaction mixture for 1 minute, and a solution prepared by dissolving thiourea (34.1 mg, 0.448 mmol) in methanol (4 mL) was added thereto at −78° C. Subsequently, the reaction mixture was stirred for 30 minutes at −78° C. and for 1 hour at 0° C. and filtered through Celite. The filtrate was dried under reduced pressure, and the residue was dissolved in methanol (7.46 mL).

Subsequently, 1,4-dioxane (4.0 M, 7.46 mL, 29.8 mmol) containing hydrochloric acid was added to the mixture at 0° C., and the mixture thus obtained was stirred for 6 hours at room temperature. The liquid was dried under reduced pressure, and the residue was suspended in THF (5 mL).

Subsequently, a saturated aqueous solution of sodium hydrogen carbonate (5 mL) and di(tert-butyl) dicarbonate (325 mg, 1.49 mmol) were added to the mixture at 0° C. The reaction mixture was stirred for 60 hours at room temperature and then diluted with water. Subsequently, the mixture was extracted with ethyl acetate, and the organic layer was separated. The organic layer was dried over sodium sulfate, then filtered, and concentrated under reduced pressure, thereby obtaining a crude product. The crude product was separated (developing solvent: ethyl acetate/hexane=6/14) by silica gel thin layer chromatography, thereby obtaining the colorless oily N-Boc-phenylalanine methyl ester 4s (72.9 mg, 70% yield, 87% ee).

(S)-Methyl 2-((tert-butoxycarbonyl)amino)-3-phenylpropanoate (4s) [87% ee]

HPLC (CHIRALPAK IB-3, i-PrOH/hexane=1/49, flow rate=0.75 mL/min): tR=12.3 min (6.6%), tR=14.4 min (93.4%);

[α]D25 +39.5 (c 1.13, CHCl3).

Incidentally, the product included the specific optical rotation, and the spectroscopic data thereof was consistent with the literature data.

Hydrolysis of di(1-naphthyl)methyl Methyl Ether

An aqueous solution of sulfonic acid (2 M, 3.2 mL, 6.4 mmol) was added to a solution prepared by dissolving di(1-naphthyl)methyl methyl ether (119 mg, 0.399 mmol) in 1,4-dioxane (6.4 mL) at room temperature. The reaction mixture was heated for 4 hours at 80° C., and water was added thereto at room temperature. Subsequently, the mixture was extracted with ethyl acetate, and the organic layer was separated. The organic layer was dried over sodium sulfate, then filtered, and concentrated under reduced pressure, thereby obtaining a crude product. The crude product was separated (developing solvent: ethyl acetate/hexane=1/3) by silica gel thin layer chromatography, thereby obtaining the colorless solid di(1-naphthyl)methanol (105 mg, 92% yield). Incidentally, the spectroscopic data of di(1-naphthyl)methanol was consistent with the literature data.

Test Example 8: Synthesis of Indolidizine Derivative Using Optically Active Carboxylic Acid di(1-naphthyl)methyl Ester

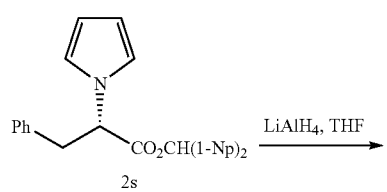

(eq. 4)

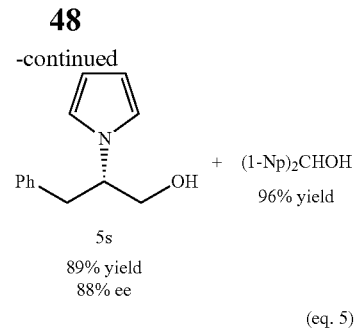

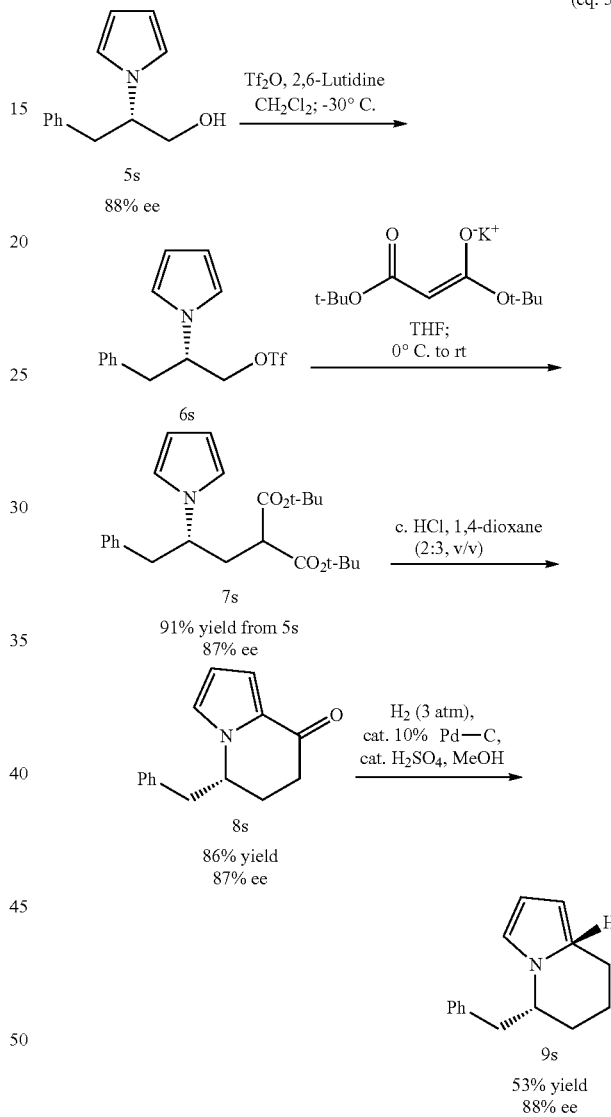

As illustrated in the reaction formula above, it was possible to synthesize an indolidizine derivative 9s by using the optically active carboxylic acid di(1-naphthyl)methyl ester 2s (87% ee) obtained by the method which conforms to Test Example 6 (reaction conditions: (1-Np)2CHOH (1.1 eq), Piv2O (3.6 eq), i-Pr2NEt (4.8 eq), (R)-BTM (5 mol %), and DMF (0.2 M) were reacted at room temperature for 24 hours) as the starting material.

By reducing the carboxylic acid di(1-naphthyl)methyl ester 2s, an optically active alcohol 5s was obtained at 89% yield, and di(1-naphthyl)methanol was recovered at 96% yield at the same time (Equation 4). Subsequently, the corresponding trifluoromethanesulfonate 6s was alkylated with a potassium salt of di(tert-butyl) malonate, the two-carbon extension conversion of the optically active alcohol 5s was conducted to obtain a dicarboxylic acid tert-butyl diester 7s from the optically active alcohol 5s at 91% yield (Equation 5). Subsequently, the dicarboxylic acid tert-butyl diester 7s was subjected to decarboxylation and intramolecular Friedel-Crafts acylation to obtain a 6,7-dihydroindolidizine-8(5H)-one derivative 8s, and this was hydrogenated with palladium on carbon to obtain the indolidizine derivative 9s as a single diastereomer. Incidentally, the enantiomer excess of the intermediate and the product 9s was maintained even during a series of conversions.

The details of each reaction are as follows.

Conversion of Carboxylic Acid di(1-naphthyl)methyl ester 2s into Optically Active Alcohol 5s LiAlO4 (46.3 mg, 1.22 mmol) was added at 0° C. to a solution prepared by dissolving the carboxylic acid di(1-naphthyl)methyl ester 2s (87% ee, 196 mg, 0.407 mmol) in tetrahydrofuran (THF) (8.1 mL). The reaction mixture was stirred for 3 hours at room temperature, water (60 μL) and an aqueous solution of sodium hydroxide (4.2 M, 60 μL) were added thereto at 0° C. The mixture was filtered through a short Celite pad together with ethyl acetate, and the filtrate was concentrated under reduced pressure, thereby obtaining a crude product. The crude product was separated (developing solvent: ethyl acetate/hexane=9/11) by silica gel thin layer chromatography, thereby recovering di(1-naphthyl) methanol (111 mg, 96% yield) as well as obtaining a colorless oily optically active alcohol 5s (73.0 mg, 89% yield, 88% ee).

(S)-3-Phenyl-2-(1H-pyrrol-1-yl)propan-1-ol (5s) [88% ee]

HPLC (CHIRALPAK AD-H, i-PrOH/hexane=1/49, flow rate=0.75 mL/min): tR=25.4 min (93.9%), tR=37.4 min (6.1%);
[α]D27-85.3 (c 1.05, CHCl3);
IR (neat): 3467, 3028, 2943, 2877, 1604, 1493, 725, 702, 636 cm-1;
1H NMR (CDCl3): δ
7.34-7.13 (m, 3H, Ar),
7.08-6.94 (m, 2H, Ar),
6.70 (t, J=2.0 Hz, 2H, pyrrole),
6.17 (t, J=2.0 Hz, 2H, pyrrole),
4.20 (tt, J=7.6, 6.0 Hz, 1H, 2-H),
3.83 (dd, J=6.4, 6.0 Hz, 2H, 1-CH2),
3.06 (d, J=7.6 Hz, 2H, 3-CH2),
1.47 (t, J=6.4 Hz, 1H, OH);
13C NMR (CDCl3): δ137.5, 128.8, 128.5, 126.6, 119.2 (pyrrole), 108.4 (pyrrole), 65.3, 63.5, 38.5 (3);
HR MS: calcd for C13H15NONa (M+Na+) 224.1046, found 224.1044.

Synthesis of Potassium Salt of Di(tert-butyl) Malonate

A liquid prepared by suspending potassium hydride (499 mg, 12.4 mL) in THF (6.2 mL) was added to a solution prepared by dissolving di(tert-butyl) malonate (2.76 mL, 12.4 mL) in tetrahydrofuran (THF) (22.4 mL) dropwise at 0° C. The reaction mixture was stirred for 18 hours at room temperature, and hexane (40 mL) was added thereto. Thereafter, the precipitate was filtered and dried, thereby obtaining the intended compound as a colorless solid (2.57 g, 82% yield). This compound was used in the subsequent experiment without being further purified.

Potassium di-tert-butylmalonate

Mp: 139-141° C. (THF/hexane);
1H NMR (DMSO-d6): δ
1.41 (s, 1H, 2-H),
1.27 (s, 18H, t-Bu).

Conversion of Optically Active Alcohol 5s into dicarboxylic acid tert-butyl diester 7s A liquid prepared by dissolving trifluoromethanesulfonic anhydride (70.9 μL, 0.422 mmol) in dichloromethane (4 mL) was gradually added to a solution prepared by dissolving the optically active alcohol 5s (70.8 mg, 0.352 mmol) and 2,6-lutidine (81.1 μL, 0.704 mmol) in dichloromethane (4 mL) at −30° C. The reaction mixture was stirred for 25 minutes at −30° C., and 0.5 M of hydrochloric acid (6 mL) was then added thereto. The mixture was extracted with chloroform, and the organic layer was separated. The organic layer was dried over sodium sulfate, then filtered, and concentrated under reduced pressure, thereby obtaining a crude product of trifluoromethanesulfonate 6s. The crude product was used in the subsequent experiment without being further purified.

Subsequently, a potassium salt of di(tert-butyl) malonate (134 mg, 0.528 mmol) was added to a solution prepared by dissolving the crude product of trifluoromethanesulfonate 6s in tetrahydrofuran (THF) (5 mL) at 0° C. The reaction mixture was stirred for 2 hours at 0° C. and for 12 hours at room temperature and diluted with water. The mixture was extracted with chloroform, and the organic layer was separated. The organic layer was dried over sodium sulfate, then filtered, and concentrated under reduced pressure, thereby obtaining a crude product. The crude product was separated (developing solvent: ethyl acetate/hexane=1/3) by silica gel thin layer chromatography, thereby obtaining the colorless oily dicarboxylic acid tert-butyl diester 7s (127 mg, 91% yield, 87% ee).

Di-tert-butyl (R)-2-(3-phenyl-2-(1H-pyrrol-1-yl) propyl)malonate (7s) [87% ee]

HPLC (CHIRALPAK IA-3, i-PrOH/hexane=1/200, flow rate=0.75 mL/min): tR=9.5 min (93.6%), tR=11.9 min (6.4%);
[α]D27-23.5 (c 1.05, CHCl3);
IR (neat): 2978, 2935, 1728, 1489, 1142, 849, 725 cm-1;
1H NMR (C6D6): δ
7.06-6.94 (m, 3H, Ar),
6.79-6.74 (m, 2H, Ar),
6.48 (t, J=2.0 Hz, 2H, pyrrole),
6.23 (t, J=2.0 Hz, 2H, pyrrole),
4.16 (dddd, J=11.6, 8.6, 6.0, 4.0 Hz, 1H, 2'-H),
3.07 (dd, J=10.8, 4.0 Hz, 1H, 2-H),
2.74 (dd, J=14.0, 8.6 Hz, 1H, 3'-CH2),
2.66 (dd, J=14.0, 6.0 Hz, 1H, 3'-CH2),
2.50 (ddd, J=14.4, 10.8, 4.0 Hz, 1H, 1'-CH2),
2.32 (ddd, J=14.4, 11.6, 4.0 Hz, 1H, 1'-CH2),
1.29 (s, 9H, t-Bu),
1.28 (s, 9H, t-Bu);
13C NMR (C6D6): δ168.6 (CO2t-Bu), 168.5 (CO2t-Bu), 138.4, 129.1, 128.5, 126.6, 119.0 (pyrrole), 108.8 (pyrrole), 81.1 (t-Bu), 81.0 (t-Bu), 60.0 (2'), 50.8 (2), 43.6 (3'), 35.4 (1'), 27.8 (t-Bu), 27.7 (t-Bu);

HR MS: calcd for C24H33NO4Na (M+Na+) 422.2302, found 422.2303.

Conversion of dicarboxylic acid tert-butyl diester 7s into 6,7-dihydroindolizine-8(5H)-one derivative 8s 12 M HCl (1.21 mL) was added to a solution prepared by dissolving the dicarboxylic acid tert-butyl diester 7s (121 mg, 0.303 mmol) in 1,4-dioxane (1.82 mL). The reaction mixture was stirred for 3 hours at 0° C. and for 65 hours at room temperature, and water was added thereto. The mixture was extracted with ethyl acetate, and the organic layer was separated. The organic layer was dried over sodium sulfate, then filtered, and concentrated under reduced pressure, thereby obtaining a crude product. The crude product was separated (developing solvent: ethyl acetate/hexane=1/1) by silica gel thin layer chromatography, thereby obtaining the pale yellow oily 6,7-dihydroindolizine-8(5H)-one derivative 8s (58.8 mg, 86% yield, 87% ee).

(R)-5-Benzyl-6,7-dihydroindolizin-8 (5H)-one (8s) [87% ee]

HPLC (CHIRALPAK IB-3, i-PrOH/hexane=1/9, flow rate=0.75 mL/min): tR=24.5 min (6.4%), tR=27.2 min (93.6%);
[α]D27-86.2 (c 1.02, CHCl3);
IR (neat): 3024, 2947, 1658, 1527, 1496, 748, 702 cm-1;
1H NMR (C6D6): δ
7.37-7.22 (m, 3H, Ar),
7.15-7.07 (m, 2H, Ar),
7.05 (dd, J=4.0, 2.0 Hz, 1H, pyrrole),
6.63 (dd, J=2.4, 2.0 Hz, 1H, pyrrole),
6.19 (dd, J=4.0, 2.4 Hz, 1H, pyrrole),
4.50-4.33 (dddd, J=10.4, 9.6, 7.6, 7.2 Hz, 1H, 5-H),
3.22 (dd, J=13.6, 7.2 Hz, 1H, CH2Ph),
3.00 (dd, J=13.6, 7.6 Hz, 1H, CH2Ph),
2.73 (ddd, J=18.0, 11.2, 5.2 Hz, 1H, 7-CH2),
2.52 (ddd, J=18.0, 5.2, 4.8 Hz, 1H, 7-CH2),
2.32 (dddd, J=11.2, 10.8, 9.6, 4.8 Hz, 1H, 6-CH2),
2.13 (dddd, J=10.8, 10.4, 5.2, 5.2 Hz, 1H, 6-CH2);
13C NMR (C6D6): δ186.8, 136.9, 130.0, 129.1, 128.8, 127.1, 125.4, 114.5, 110.1, 56.1 (5), 41.2 (7), 32.8 (CH2Ph), 27.4 (6);
HR MS: calcd for C15H15NONa (M+Na+) 248.1078, found 248.1086.

Conversion of 6,7-dihydroindolizine-8(5H)-one Derivative 8s into Indolidizine Derivative 9s Palladium on carbon (supported at 10%, 50 mass %, 450 mg, 0.211 mmol) was added to a solution prepared by dissolving the 6,7-dihydroindolizine-8(5H)-one derivative 8s (59.6 mg, 0.246 mmol) and sulfuric acid (10 μL) in methanol (5.3 mL). The mixture was stirred for 4 days at room temperature in a hydrogen atmosphere at 3 atm and then purged with argon. The mixture was filtered through a short Celite pad, and the filtrate was concentrated under reduced pressure. The residue was diluted with 1 M hydrochloric acid (3 mL) and washed with ethyl acetate. The aqueous layer was basified with an aqueous solution of sodium hydroxide (4.2 M, 2 mL) and then extracted with chloroform, and the organic layer was separated. The organic layer was dried over sodium sulfate, then filtered, and concentrated under reduced pressure, thereby obtaining a crude product. The crude product was separated (developing solvent: 28% aqueous ammonia/methanol/chloroform=2/3/95) by silica gel thin layer chromatography, thereby obtaining the colorless oily indolidizine derivative 9s (31.1 mg, 53% yield, 88% ee).

(5R,8aS)-5-Benzyloctahydroindolizine (9s) [88% ee]

HPLC (CHIRALCEL OJ-H×2, diethylamine/i-PrOH/hexane=0.2/1/100, flow rate=0.5 mL/min): tR=16.7 min (93.9%), tR=27.2 min (6.1%);
[α]D24 +66.4 (c 1.01, CHCl3);
IR (neat): 3024, 2931, 2862, 1604, 1496, 1126, 748 cm-1;
1H NMR (C6D6): δ
7.25-7.04 (m, 5H, Ar),
3.26 (ddd, J=8.8, 8.8, 2.2 Hz, 1H, 3-CH2),
3.07 (dd, J=13.0, 4.0 Hz, 1H, CH2Ph),
2.48 (dd, J=13.0, 9.6 Hz, 1H, CH2Ph),
2.15 (dddd, J=13.2, 9.6, 4.0, 2.4 Hz, 1H, 5-CH2),
1.94 (ddd, J=8.8, 8.8, 8.8 Hz, 1H, 3-CH2),
1.80-1.33 (m, 8H, 1-CH2, 2-CH2, 6-CH2, 8-CH2, 8a-H),
1.27-0.96 (m, 3H, 6-CH2, 7-CH2);
13C NMR (C6D6): δ140.2, 129.9, 128.4, 126.1, 65.2, 65.0, 52.0, 42.1, 31.4, 31.3, 31.2, 25.0, 21.0;
HR MS: calcd for C15H22N (M+H+) 216.1747, found 216.1744.

The invention claimed is:

1. A method for producing an optically active carboxylic acid ester by dynamic kinetic resolution, the method comprising a step of racemizing the other enantiomer of racemic carboxylic acids represented by the following formula (a):

[in formula (a), $R^{a1}$ represents a nitrogen-containing heteroaromatic ring group bonded to an asymmetric carbon via a nitrogen atom constituting a ring, and $R^{a2}$ represents an organic group]

as well as selectively esterifying one enantiomer of the racemic carboxylic acids by reacting the racemic carboxylic acids with an alcohol represented by the following formula (b):

[in formula (b), $R^b$ represents a phenyl group, naphthyl group, anthryl group, or phenanthryl group which optionally has a substituent]

or a phenol derivative represented by the following formula (c):

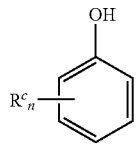
(c)

[in formula (c), $R^c$ represents a phenyl group, naphthyl group, anthryl group, or phenanthryl group which optionally has a substituent, and n represents an integer from 1 to 5, $R^c$s may be the same as or different from one another in a case in which there are a plurality of $R^c$s]
in a polar solvent having a dipole moment of 3.5 or more in the presence of an acid anhydride and an asymmetric catalyst.

2. The method for producing an optically active carboxylic acid ester according to claim 1, wherein the asymmetric catalyst is represented by any one of the following formulas (d) to (g):

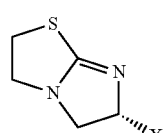
(d)

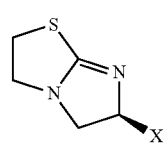
(e)

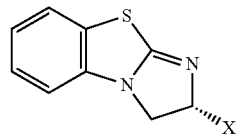
(f)

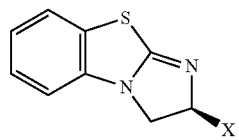
(g)

[in formulas (d) to (g), X represents any one of the following substituents,

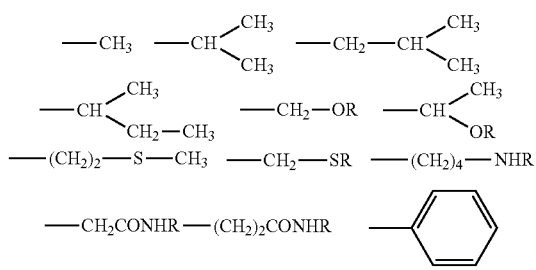

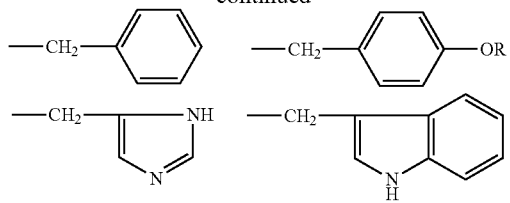

and R represents a protective group of a hydroxyl group].

3. The method for producing an optically active carboxylic acid ester according to claim 1, wherein $R^{a1}$ in formula (a) is a 1H-pyrrol-1-yl group.

4. The method for producing an optically active carboxylic acid ester according to claim 1, wherein the polar solvent having a dipole moment of 3.5 or more is dimethylacetamide, dimethylformamide, 1,3-dimethyl-2-imidazolidinone, N-methylpyrrolidone, or dimethyl sulfoxide.

5. The method for producing an optically active carboxylic acid ester according to claim 1, wherein the step is performed in the presence of a base.

6. The method for producing an optically active carboxylic acid ester according to claim 5, wherein the base is represented by the following formula (i):

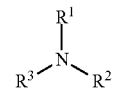

[in formula (i), $R^1$, $R^2$, and $R^3$ independently represent an alkyl group having from 1 to 8 carbon atoms].

7. The method for producing an optically active carboxylic acid ester according to claim 6, wherein at least one of $R^1$, $R^2$, or $R^3$ is a methyl group.

8. The method for producing an optically active carboxylic acid ester according to claim 6, wherein the base is diisopropylethylamine, triethylamine, dimethylethylamine, dimethylisopropylamine, diethylmethylamine, or diisopropylmethylamine.

9. The method for producing an optically active carboxylic acid ester according to claim 1, further comprising a step of obtaining racemic carboxylic acids represented by formula (a) by converting an amino group of racemic α-amino acids represented by the following formula (h):

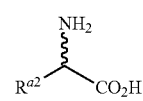
(h)

[in formula (h), $R^{a2}$ is synonymous with that in formula (a)]
into a 1H-pyrrol-1-yl group.

10. The method for producing an optically active carboxylic acid ester according to claim 1, further comprising a step of converting a 1H-pyrrol-1-yl group of an optically active carboxylic acid ester obtained by dynamic kinetic resolution into an amino group.

* * * * *